US006849430B2

(12) United States Patent
Carson et al.

(10) Patent No.: US 6,849,430 B2
(45) Date of Patent: Feb. 1, 2005

(54) PCR-BASED MONITORING IN WASTEWATER BIOTREATMENT SYSTEMS

(75) Inventors: David B. Carson, St. Louis, MO (US); James F. Rice, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 462 days.

(21) Appl. No.: 10/128,781

(22) Filed: Apr. 23, 2002

(65) Prior Publication Data

US 2003/0092020 A1 May 15, 2003

Related U.S. Application Data

(60) Provisional application No. 60/285,846, filed on Apr. 23, 2001.

(51) Int. Cl.$^7$ .......................... C12P 19/34; C12Q 1/68; C07H 21/04
(52) U.S. Cl. ................. 435/91.2; 435/91.1; 435/91.21; 435/6; 536/23.1; 536/24.33; 536/24.3
(58) Field of Search .............................. 435/91.2, 91.1, 435/6; 536/23.1, 24.3, 24.33

(56) References Cited

U.S. PATENT DOCUMENTS

| | | |
|---|---|---|
| 4,683,202 A | 7/1987 | Mullis |
| 4,851,131 A | 7/1989 | Grabiak et al. |
| 5,213,961 A | 5/1993 | Bunn et al. |
| 5,298,392 A | 3/1994 | Atlas et al. |
| 5,463,175 A | 10/1995 | Barry et al. |
| 5,540,840 A | 7/1996 | Heitkamp et al. |
| 5,705,332 A | 1/1998 | Roll |
| 5,776,760 A | 7/1998 | Barry et al. |
| 5,792,650 A | 8/1998 | Ohtake et al. |
| 5,837,501 A | 11/1998 | Beumer et al. |
| 5,888,740 A | 3/1999 | Han |
| 6,106,718 A | 8/2000 | Maneshin et al. |
| 6,110,661 A | 8/2000 | Lajoie et al. |

FOREIGN PATENT DOCUMENTS

| | | |
|---|---|---|
| JP | 10201499 | 8/1998 |
| WO | WO-99/14359 | 3/1999 |

OTHER PUBLICATIONS

Watanabe et al. Population Dynamics of Phenol–degrading Bacteria in Activated Sludge Determined by gyrB–Targeted quantitative PCR, Applied and Environment microbiology, vol. 64, No. 4, pp. 1203–1209, Apr. 1998.*
Lee et al. Estimation of the Abundance of an Uncultured soil bacterial strain by a competitive quantitative PCR method. Applied Environmental microbiology. vol. 62, No. 10, pp. 3787–3793, Oct. 1996.*
Adams Jr. et al., *Development of Design and Operational Criteria for Wastewater Treatment*, 1981, EnviroPress Inc., Nashville, TN.

Tchobanoglous, G., et al., *Wastewate Engineering: Treatment, Disposal, and Reuse*, 3rd Edition, 1991, Melcalf & Eddy, Inc., McGraw–Hill.

Hallas et al., Glyphosate Degradation by Immobilized Bacteria: Field Studies with Industrial Wastewater Effluent, *Appl. Environ. Microbiol.*, 1992, pp. 1215–1219, vol. 58, No. 4.

Heitkamp et al., Glyphosate degradation by immobilized bacteria: laboratory studies showing feasibility fro glyphosate removal from waste water, *Can. J. Microbiol.*, 1992, pp. 921–928, vol. 38.

ERB et al., Detection of Polychlorinated Biphenyl Degradation Genes in Polluted Sediments by Direct DNA Extraction and Polymerase Chain Reaction, *Appl. Environ. Microbiol.*, 1993, pp. 4065–4073, vol. 59, No. 12.

Fleming et al., Quantitative Relationship between Naphthalene Catabloic Gene Frequency and Expression in Prediciting PAH Degradation in Soils at town Gas Manufacturing Sites, *Environ. Sci. Technol.*, 1993, pp. 1068–1074, vol. 27, No. 6.

Herrick et al., Polymerase Chain Reaction Amplification of Naphthalene–Catabolic and 16S rRNA Gene Sequences from indigenous Sediment Bacteria, *Appl. Environ. Microbiol.*, 1993, pp. 687–694, vol. 59, No. 3.

Hallas et al., Microbial Treatment of Chemical Process Wastewater, *Microbial Transformation and Degradation of Toxic Organic Chemicals*, 1995, pp. 349–387, Wiley–Liss, Inc., NY.

Joshi et al., Detection of metapyrocatechase homologous genes in petroleum hydrocarbon contaminated groundwater by polymerase chain reaction, *J. Microbiol. Meth.*, 1996, pp. 121–128, vol. 27.

(List continued on next page.)

*Primary Examiner*—Kenneth R. Horlick
*Assistant Examiner*—Cynthia Wilder
(74) *Attorney, Agent, or Firm*—Joseph A. Schaper; Harness, Dickey & Pierce, P.L.C.

(57) ABSTRACT

PCR-based monitoring of microorganisms in systems for the biological treatment of wastewater. In particular, measuring both the abundance and expression of indicator/effector genes or gene combinations, where expression of an "effector" gene correlates with the degradative activity of a particular microbial sample, and where the abundance of an "indicator" gene correlates with the abundance of microbe. Effector gene expression is measured by competitive quantitative RT-PCR, and indicator gene abundance is measured by competitive quantitative PCR. The indicator and effector genes may be the same or different genes. In one embodiment, the indicator and effector gene are sequences from the glyphosate oxidoreductase (gox) gene and the quantitative techniques employed are competitive quantitative PCR and competitive quantitative RT-PCR.

13 Claims, 4 Drawing Sheets

OTHER PUBLICATIONS

Joshi et al., PCR amplification of catechol 2,3-dioxygenase gene sequences from naturally occuring hydrocarbon degrading bacterial isolated from petroleum hydrocarbon contaminated groundwater, *FEMS Microbiol. Ecol.*, 1996, pp. 5–15, vol. 19.

Lee et al., Estimation of the Abundance of an Uncultured Soil Bacterial Strain by a Competitive Quantitative PCR Method, *Appl. Environ. Microbiol.*, 1996, pp. 3787–3793, vol. 62, No. 10.

Pazirandeh et al., Development of Bacterium–Based Heavy Metal Biosorbents: Enhanced Uptake of Cadmium and Mercury by *Escherichia coli* Expressing Metal Binding Motif, *Appl. Environ. Microbiol.*, 1998, pp. 4058–4072, vol. 64, No. 10.

Ducroco et al., The use of quantitative PCR, plant and earthworm bioassays, plating and chemical analysis to monitor 4-chlorobiphenyl biodegradation in soil microcosms, *Appl. Soil Ecol.*, 1999, pp. 15–27, vol. 12.

Freeman et al., Quantitative RT–PCR: Pitfalls and Potential, *BioTechniques*, 1999, pp. 112–125, vol. 26–1.

Hao et al., Cloning, Expression, and Characterization of Cadmium and Manganese Uptake Genes from *Lactobacillus plantarum*, *Appl. Environ. Microbiol.*, 1999, pp. 4746–4752, vol. 65, No. 11.

Watanabe et al., An Outbreak of Nonflocculating Catabolic Populations Caused the Breakdown of a Phenol–Digesting Activated–Sludge Process, *Appl. Environ. Microbiol.*, 1999, pp. 2813–2819, vol. 65, No. 7.

Mesarch et al., Development of Catechol 2,3-Dioxygenase-Specific Primers for Monitoring Bioremediation by Competitive Quantitative PCR, *Appl. Environ. Microbiol.*, 2000, pp. 678–683, vol. 66, No. 2.

Ravel et al., Cloning and Sequence Analysis of the Mercury Resistance Operon of *Streptomyces sp.* Strain CHR28 Reveals a Novel Putative Second Regulatory Gene, *J. Bacteriol.*, 2000, pp. 2345–2349, vol. 182, No. 8.

Watanabe et al., Starvation improves Survival of Bacteria Introduced into Activated Sludge, *Appl. Environ. Microbiol.*, 2000, pp. 3905–3910, vol. 66, No. 9.

Dionisi et al., Quantification of *Nitrosomonas oligotropha*-Like Ammonia–Oxidizing Bacteria and *Nitrospira* spp. from Full–scale Wastewater Treatment Plants by competitive PCR, *Appl. Environ. Microbiol.*, 2002, pp. 245–253, vol. 68, No. 1.

Roish et al., The mechanism of action of the herbicide N-(phosphonomethyl) glycine: its effects on the growth and the enzymes of aromatic amino acid biosynthesis in *Escherichia coli, Hoppe Seylers Z Physiol. Chem.*, 1980, pp. 1049–1058, vol. 361, No. 7, Abstract Only.

Shinabarger et al., Glyphosate catabolism by *Pseudomonas* sp. strain PG2982, J. Bacteriol., 1986, pp. 702–707, vol. 168, No. 2, Abstract Only.

Monpoeho et al., Quantification of Enterovirus RNA in Sludge Samples Using Single Tube Real–Time RT–PCR, *Bio Techniques*, date unknown, pp. 88–93, vol. 29, Abstract Only.

Fille et al., Quantitative RT–PCR Using a PCR–Generated Competitive Internal Standard, *Bio Techniques*, 1997, pp. 34–46, vol. 23, No. 1.

Klebe et al., RT–PCR Without RNA Isolation, Bio Techniques, date unknown, pp. 1094–1100, vol. 21, Abstract Only.

Drebot et al., RT–PCR Detection of RNA Viruses in Stool Specimens, Bio Techniques, 1997, pp. 616–619, vol. 23, No. 4.

Delarue et al., Correcting for Different Amplification Rates of Internal Standard nad Template when Measuring cDNA by Competitive PCR, Bio Techniques, 2000, pp. 396–398, vol. 28, No. 3.

Watanabe et al., "Population of Phenol–Degrading Bacteria in Activated Sludge Determinded by gyrB–Targeted Quantitative PCR," Appl. Environ. Microbiol., 1998, pp. 1203–1209, vol. 64:4.

International Search Report, Apr. 3, 2003.

* cited by examiner

PCR-BASED MONITORING IN WASTEWATER BIOTREATMENT SYSTEMS

PRIOR RELATED APPLICATIONS

This application claims priority to prior U.S. Provisional Patent Application Ser. No. 60/285,846, filed Apr. 23, 2001, which is incorporated herein by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to PCR-based monitoring of microorganisms in systems for the biological treatment of wastewater. In particular, the invention relates to measuring both the abundance and expression of indicator/effector genes or gene combinations, where expression of an "effector" gene correlates with the degradative activity of a particular microbial sample, and where the abundance of an "indicator" gene correlates with microbial abundance. Effector gene expression is measured by quantitative RT-PCR, and indicator gene abundance is measured by quantitative PCR. The indicator and effector genes may be the same or different genes.

While expression of the glyphosate oxidoreductase (gox) gene (U.S. Pat. No. 5,463,175, U.S. Pat. No. 5,776,760) in an activated sludge-based system is used to exemplify such PCR-based monitoring, invention embodiments may be broadly utilized with any indicator/effector gene combination and in any system that utilizes the catabolic activity of microorganisms for biological treatment of wastewater. The invention also relates to methods for the active control of wastewater biotreatment systems based on information derived from such PCR-based monitoring.

BACKGROUND OF THE INVENTION

Biotreatment of organic waste has been used for centuries as a means of modifying ecosystems. Composting, for example, has been used from the dawn of agriculture as a way to produce soil amendments from organic waste and to enhance nutrient cycling. In this century, biotreatment of wastewater has also been used as a way to remove organic matter (U.S. Pat. No. 5,540,840), as well as to facilitate water reclamation through various other means (U.S. Pat. No. 5,792,650).

Most existing wastewater treatment plants were built decades ago at a time when less stringent water quality standards (e.g., those based on criteria like biological oxygen demand (BOD) and chemical oxygen demand (COD)) were in place. Furthermore, these wastewater treatment plants commonly relied on activated sludge processes as a core component of wastewater biotreatment. While treatment systems that utilize only physio-chemical processes are available for water reclamation (U.S. Pat. No. 4,851,131), activated sludge-based systems remain as standards, particularly for aerobic wastewater treatment systems (Hallas, Laurence E. and Michael A. Heitkamp, 1995. "Microbiological treatment of chemical process wastewater." In: Young, Lily Y. and Carl E. Cerniglia (eds) *Microbial Transformation and Degradation of Toxic Organic Chemicals*, New York: Wiley-Liss, pp. 349–387).

Though improvements in component unit processes of wastewater biotreatment systems have been made, translating these improvements into consistent realization of higher quality effluents has been hampered by the need to rely on monitoring processes that permit only slow or passive adjustments in control processes. For some narrowly circumscribed situations, however, monitoring technology has progressed to approach real-time control of unit processes in wastewater biotreatment systems. For example, NADH fluorescence and pH signals may be utilized to optimize the rate of carbonaceous nutrient feeding to a anoxic reactor (U.S. Pat. No. 6,106,718), or, as another example, the level of expression by reporter bacteria of a gene encoding a bioluminescent reporter protein may be monitored photometrically as being correlative with the absence or presence of bacteriocidal toxicity in a wastewater treatment stream (U.S. Pat. No. 6,110,661).

In general, technologies for monitoring the abundance and expression of genes encoding proteins that mediate the microbial degradation of target components of wastewater treatment streams have been lacking. Methods that permit informed, active control of wastewater biotreatment systems through the utilization of information derived from such monitoring have also been lacking. The present invention overcomes these and other deficiencies in the prior art and meets a long-felt need for technology to accomplish monitoring of both the abundance and expression of key microbial genes, so as to permit active control of wastewater biotreatment systems.

Wastewater treatment, whether for municipal or industrial wastewater, has generally been pursued as a battery of treatments that may be divided into three general levels: primary, secondary, and tertiary. Primary treatment typically involves the removal of a substantial amount of suspended solids from a wastewater sample. A principle technology for primary treatment is sedimentation. During sedimentation, settleable solids are removed from raw wastewaters. For organic industrial discharges with a low-to-moderate suspended solids content, passage through an equalization basin may be required if the organic matter content or hydraulic flow rate of the wastewater varies appreciably over time.

Secondary treatment may be viewed as generally being bioremedial in nature. It usually consists of bio-oxidizing those organic solids that remain after primary treatment has been completed. Commonly used technologies in the secondary treatment of primary effluent rely on suspended growth biotreatments, and particularly, on activated sludge processes. Although secondary treatment systems and their component unit operations and processes have been the loci of key technological advances in recent decades, limitations in monitoring processes often prevent active control processes from being implemented in many secondary treatment systems.

Typically aerobic secondary, and often tertiary, treatment occurs in biological reactor systems. These fall into two general categories—aerobic suspended growth and attached growth systems. In either case, the principle is the same: to bring microbial biomass in contact with (i) organic compounds as a source of energy, (ii) an electron acceptor (like oxygen or nitrate), and (iii) appropriate nutrients for microbial growth. As organic components are degraded, a means to separate the treated liquor from the increased biomass must be provided.

In aerobic systems, the technology of continuous flow activated sludge has been the mainstay technology of secondary treatment. In a continuous flow activated sludge system, as depicted in FIG. 1, waste is first mixed and aerated with microorganisms in an aeration tank 50 for a defined period of time. A second tank, a clarifier 60, provides for separation (i.e., clarification) of water with a greatly reduced organic (sometimes inorganic) content from biomass that settles into an activated sludge blanket 65.

Despite passage through well-tested secondary treatment processes, aqueous discharges from secondary treatment systems may not meet water quality standards. Levels of suspended solids, nutrients, or specific regulated compounds in such aqueous discharges may be unacceptable. In such cases, tertiary treatment is required. Tertiary treatment options include additional chemical treatment (e.g., activated carbon filtration, ozonation, coagulation, air stripping, and ion exchange processing) and/or biological treatment (e.g., polishing components with specific microbes on activated carbon or alginate).

As might be expected, continuous flow activated sludge processes are mechanically well understood. Key operating variables are used to design and operate systems successfully. For example, initial waste characterization is followed by reactor sampling in order to define operational system organic loadings (food/microorganism or F/M ratios). In addition, rates of air delivery and oxygen transfer are determined and adjusted to achieve desired levels of wastewater processing. Finally, the making of similar determinations and adjustments for rates of clarification, as well as of microorganism growth (and subsequent biomass wastage) are made. Various augmentations of component unit processes may also be used in order to improve continuous flow activated sludge systems. For example, the addition of activated carbon to the aeration tank has provided a successful variation in treating dilute but variable wastewater.

In wastewater biotreatment systems monitoring methods are required to detect and maintain process stream parameters within optimal ranges or, at least, to prevent catastrophic perturbations in the operation of such systems and to avoid excursions beyond water quality limits. In addition to microorganism diversity, the level of constant solids, F/M ratio, mean cell retention time (MCRT), settling rate and sludge volume index, as well as oxygen uptake rate (OUR) and specific oxygen uptake rate, are among the process control parameters measured in wastewater biotreatment systems.

This type of information is helpful in deciding what adjustments should be made, e.g., in channeling return activated sludge flow versus waste activated sludge flow (see, respectively, 67 and 69 of FIG. 1; see also, *Wastewater Engineering: Treatment, Disposal, and Reuse* (McGraw-Hill Series in Water Resources and Environmental Engineering, 1991) by George Tchobanoglous, Franklin L. Burton, and Metcalf & Eddy, Inc. Staff).

Biological oxygen demand (BOD) is the amount of oxygen that would be consumed if all the organic material in one liter of water were oxidized by microorganisms. In a rudimentary method of measuring five-day BOD ($BOD_5$), two equal volumes of water are sampled from a test pool and each aliquot is diluted with a known volume of distilled water which has been thoroughly shaken to insure oxygen saturation. The concentration of oxygen within one of the aliquots is then measured using an oxygen meter, while the remaining aliquot is sealed and placed in total darkness. Five days later, the concentration of oxygen within the second aliquot is measured using an oxygen meter. $BOD_5$ is determined by subtracting the second meter reading from the first.

The greater the relative amount of organic matter to be oxidized, the greater the relative amount of oxygen that will be needed by microorganisms within a wastewater biotreatment system in order to oxidize that amount of organic matter. Furthermore, $BOD_5$ is heavily influenced by the microorganism seed source and the degree of acclimation of sample microorganisms to waste components to be used as substrates in measuring $BOD_5$. As a result of these relationships, $BOD_5$ can be used to measure wastewater biotreatment efficiencies for specific substrates. For example, formaldehyde in wastewater of certain types may be bio-oxidized by activated sludges of various kinds and thus be detectable as $BOD_5$. However, degradation of glyphosate (i.e., N-phosphonomethylglycine) and N-phosphonomethyliminodiacetic acid (PIA) from the same wastewater may not be detectable as $BOD_5$ if there are no gox-expressing microorganisms in the activated sludge.

Alternatively, oxygen demand can be measured using a chemical oxidizing agent. This is called chemical oxygen demand (COD). COD may be expressed in terms of the milligrams of oxygen required to chemically oxidize the organic contaminants in one liter of wastewater. COD values are generally higher than BOD values. Typical COD values for domestic wastewater range from 200 to 500 mg/L. COD provides an indication of the theoretical oxygen demand and is often used in place of BOD, particularly because COD determinations may be established after only a few hours, while standard $BOD_5$ determinations require five days.

Determining total organic carbon (TOC) levels in wastewater has been used for many years as a method for estimating pollution levels. Several methods may be utilized to measure wastewater TOC, though all methods typically measure the organic carbon content of aqueous samples. Typical TOC values for domestic wastewater range from 100 to 300 mg/L.

Mean cell residence time (MCRT) is the length of time that the average microorganism remains in a treatment process (e.g., a continuous flow activated sludge process) considering the removal of microorganisms (e.g., via the sludge wasting process). MCRT may also be expressed in terms of solids retention time or sludge age. For example, if five days on average are required for the removal of an amount of sludge equal to that typically held in a system, sludge microorganisms will remain in the sludge contained in the system for an average of five days. Accordingly, the sludge age for the treatment process would be five days. For a typical plant through which domestic wastewater is treated by a conventional activated sludge process, a typical range for MCRT would be five to fifteen days. For a plant handling industrial wastewater, a typical range would be 30 to 100 days.

Microorganism diversity profiles in biotreatment systems change with environmental conditions, including dissolved oxygen concentration and hydraulic residence times (HRTs). HRT refers to the average time an aqueous or fluid phase of a biotreatment system remains within the system. MCRT and HRT may differ markedly for some systems, e.g., those utilizing immobilized bacteria technology. Complete mix activated sludge systems provide another example of MCRT and HRT differences. It is common for industrial biological systems employing complete mix activated sludge systems to possess a HRT of 2–7 days, but a MCRT of 30–80 days.

In most systems, however, as HRT increases, more substrate organic matter is sorbed (i.e., both absorbed and adsorbed) as well as biologically degraded by microorganisms. Consequently, the ratio of substrate organic matter to microorganism biomass (i.e., the F/M ratio) decreases, which can dramatically change the structure of the microorganism community.

Mixed liquor volatile suspended solids (MLVSS) includes living and nonliving organic matter and represents a crude approximation of the amount of biomass. Mixed liquor suspended solids (MLSS) also includes inorganic solids and thus is a more crude estimate of biomass. Typically, MLVSS is 70 to 80% of MLSS.

The F/M ratio is also important in maintaining a biotreatment system. Since BOD (or COD) times influent (or exfluent) flow rates is an estimate of the numerator F, and MLVSS is an estimate of the denominator M, BOD (or COD) times influent (or effluent) flow rate per unit of MLVSS provides an estimate of the F/M ratio.

Although these parameters have been successfully used to monitor biological waste treatments systems, they suffer disadvantages. In particular, the measurement of MLVSS is only an approximation of total biological content and further includes all of the organisms found in an activated sludge. These are usually quite diverse and may include bacteria, protozoa, rotifers, fungi, and nematodes, as well as algae and insect larvae. In addition, the MLVSS measurements do not distinguish between living versus nonliving microorganisms.

The primary way that microbial activity has been monitored for a given MLVSS value is by conducting non-specific oxygen uptake rate (OUR) analyses. However, such analyses reflect degradative microbial activity for multiple components of a wastewater sample as opposed to a single component, such as glyphosate. Oxygen uptake rates are also greatly influenced by the presence or absence of more readily degradable components in a wastewater sample.

The dynamics of changes in microbial community structure and the performance of wastewater biotreatment systems are closely related. Thus, an efficient means of accurately quantifying those organisms responsible for specific biological processes would be of considerable benefit in water reclamation because it would allow finer monitoring and control of the wastewater biotreatment systems. It is particularly desirable to monitor the structure of bacterial and other microorganism communities in a way that does not rely on cell culture methods in order to determine not only the type of microorganisms responsible for the degradation of a specific regulated compounds, but also their abundance and activity.

PCR-based methods (U.S. Pat. No. 4,683,202 and US patents citing same) have been useful for detecting genes from microorganisms involved in the degradation of xenobiotic compounds. For example, DNA extraction followed by PCR has been used to detect genes of microorganisms important in the degradation of polychlorinated biphenyl organics (Erb et al., 1993, Appl. Environ. Microbiol. 59: 4065–4073) and naphthalene (Herrick et al., 1993, Appl. Environ. Microbiol. 69: 687–694) in polluted sediments, as well as other genes, including catechol 2,3-dioxygenase genes (Joshi and Walia, 1996, FEMS Microbiol. Ecol. 19: 5–15) and metapyrocatechase homologous genes (Joshi and Walia, 1996, J. Microbiol. Methods 27: 121–128) in petroleum hydrocarbon contaminated groundwater.

PCR-based methods have been used not only to detect, but also to quantitatively estimate, soil bacteria degrading 4-chlorobiphenyl organics (Ducrocq et al., 1999, Appl. Soil. Ecol. 12: 15–27) as well as an uncultured bacterial strain (Lee et al., 1996, Appl. Environ. Microbiol. 62: 3787–3793). Methods of quantitative PCR (qPCR), particularly competitive qPCR (U.S. Pat. No. 5,213,961 and US patents citing same), have been used to follow fluctuations in the diversity of bacterial populations in phenol-acclimated activated sludge (Watanabe et al., 1999, Appl. Environ. Microbiol. 65: 2813–2819). Mesarch et al. (2000, Appl. Environ. Microbiol. 66: 678–683) developed primers specific for catechol 2,3-dioxygenase genes of certain strains of Pseudomonas bacteria so that competitive qPCR could be used in direct, non-cultivation-based techniques for enumerating microbial populations in soil samples.

Watanabe et al. (2000, Appl. Environ. Microbiol. 66:3905–3910) also used qPCR-based methods to estimate the densities of Ralstonia eutropha E2 bacteria present in activated sludge. In addition to estimating densities of R. eutropha E2 bacteria in activated sludge using qPCR with pox gene-specific primers, Watanabe et al. (2000) also used methods of reverse transcription PCR (RT-PCR) to detect, but not quantify, the expression of the pox gene by these bacteria in activated sludge. Through pox gene expression, R. eutropha E2 bacteria are capable of growing on media containing phenol as a sole carbon source. Watanabe designed and used the same pox gene-specific DNA primers for both qPCR and nonquantitative RT-PCR. Dionisi et al. (2002) recently used qPCR-based methods to enumerate ammonia- and nitrite-oxidizing bacteria from municipal and industrial activated sludge (Dionisi, H. M. et al., 2000 Appl and Environ Microbiol, Vol. 68 (1): 245–253). However, no attempt was made to determine the activity of the specific nitrifying bacterial populations.

While PCR-based methods have been shown to have utility for characterizing genes expressed in the activated sludge of wastewater biotreatment systems, monitoring methods are needed to quantify with accuracy both the relative abundance and the relative expression levels of these genes. Furthermore, operational procedures to translate both abundance and expression values derived from the monitoring methods into optimal control parameters are needed for wastewater biotreatment systems. In other words, methods of wastewater characterization that allow accurate monitoring in a near real-time manner for both the abundance and expression of indicator/effector gene combinations are needed, as are methods for using such abundance and expression determinations in order actively to control wastewater biotreatment systems for optimal water reclamation. The need for such methods (and compositions therefor) has become more pronounced with each passing year.

SUMMARY OF THE INVENTION

ABC—active bioremedial content, directly proportional to the level of effector gene RT-PCR product.

AMC—active microbe content, directly proportional to the level of indicator gene PCR product.

BOD—biological oxygen demand.

$BOD_5$—five-day biological oxygen demand.

$BOD_{gly}$—biological oxygen demand for glyphosate.

cgox—in this case: a truncated gox gene used as an internal control in competitive PCR protocols; may also be an insertional or sequence variant; other internal controls are also possible.

COD—chemical oxygen demand.

Competitive quantitative PCR—a quantitative measurement of DNA content, where an internal homologous DNA standard is used to control for variations in amplification efficiency.

Competitive quantitative RT-PCR—a quantitative measurement of RNA content, where an internal homologous RNA standard is used to control for variations in reverse transcription and amplification efficiency.

Empirically determined optimal operating range—refers to optimal ABC, AMC and SBC values as empirically pre-determined by the operator to provide the most efficient degradation of a particular wastewater component.

Effector gene—any gene, or portion thereof, that encodes a degradative enzyme of interest, preferably a rate limiting enzyme in a particular degradative pathway.

F/M—food to microorganism ratio.

$F_{BOD}$/M—food to microorganism ratio where F is measured as BOD.

GDA—glyphosate degrading activity.

gox—glyphosate oxidoreductase gene.

HRT—hydraulic residence time.

Indicator gene—any gene, or portion thereof, generally unique to the microbe of interest; may be the same as the effector gene; used to measure abundance of the microbe of interest in a population of microbes.

Internal control—exemplified in this case as homologous to the indicator and/or effector gene, but with a small size variation. A small sequence variation, such as a changed restriction endonuclease site, is also possible. Other internal controls may be employed, but homologous controls are preferred.

MCRT—mean cell retention time.

MLSS—mixed liquor suspended solids.

MLVSS—mixed liquor volatile suspended solids.

OUR—oxygen uptake rate.

PCR—polymerase chain reaction.

qPCR—quantitative PCR—quantitative PCR is exemplified herein by competitive techniques employing an internal homologous control that differs in size from the target by a small insertion or deletion. However, non-competitive and kinetic quantitative PCR may also be used. Experiments are planned to combine real-time, kinetic PCR detection together with an internal homologous control that can be simultaneously detected alongside the target sequences. Bio-Techniques 26(1):112–125(1999), for example, provides an excellent discussion of quantitative PCR, particularly as applied to RT-PCR.

qRT-PCR—quantitative reverse transcription—polymerase chain reaction, see qPCR for a description of relevant technologies that can also be applied to qRT-RCR.

RT-PCR—reverse transcription—polymerase chain reaction.

SBC—specific bioremedial content, SBC=ABC/AMC.

TOC—total organic carbon.

TMC—total microbial content, can be measured by PCR determination of a ubiquitous gene.

Broadly described, the invention is a method of monitoring a waste treatment system by sampling wastewater from a waste treatment system and collecting the solids (including the microbial population therein) from the sample by any effective means. DNA and RNA are isolated from the solids and are quantitatively amplified to determine the abundance of a particular microbe population and the level of expression of a particular degradative gene. If necessary, mRNA from eukaryotic microbes can be further purified by oligo-dT hybridization prior to amplification.

Microbial abundance is assessed by measuring the level of an "indicator" gene and degradative potential is assessed by measuring the level of expression of an "effector" gene. Indicator gene abundance correlates with the active microbial content (AMC) of said sample, and the level of expression of the effector gene correlates with the active bioremedial content (ABC). The specific bioremedial content (SBC) is the ABC divided by the AMC. The exact units are not critical and may be modified as convenient.

The waste treatment system is perturbed, for example by adding nutrients, and the process is repeated until the AMC and ABC and/or the SBC are within an empirically pre-determined optimal operating range. A high ABC indicates a high level of expression of effector gene. A very low AMC may indicate that cells have died and degraded beyond the point of detection. A high SBC indicates robust cell health and expression of the effector gene.

The method can be used to effect real-time monitoring of a waste treatment system, and thus is particularly useful for optimizing a given system because a very rapid assessment of response is possible. Further, the monitoring method is much more sensitive than presently available methods, and is also considerably more specific because live cells that actively contribute to the degradative potential are assayed.

In one embodiment, the method uses competitive quantitative PCR and competitive quantitative RT-PCR to measure indicator gene abundance and effector gene expression, respectively. However, noncompetitive, kinetic, and combination methods of qPCR and qRT-PCR may also be used. The invention is exemplified with an internal control construct that produces a size variant of the indicator/effector gene PCR product. This minimizes sequence specific PCR artifacts and helps to ensure accuracy of quantification. The competitor can be carefully tested to ensure that the small change in amplified fragment size does not significantly influence the efficiency of PCR amplification, but tests show that the small (50 bp) change in size did not noticeably contribute to cycling efficiency. Other internal controls are also possible.

The gox gene is employed herein as both the indicator and the effector gene, but other indicator genes are possible, requiring only that the indicator gene be stable in the genome and have some sequence unique to the microbe of interest. The effector gene can be any degradative gene, but preferably encodes the rate limiting gene in a given degradative pathway. Examples of other effector genes include nahAc, pox, ditAl, merP, merT, amoA and mntA genes.

The method herein is exemplified by densitometry measurement of stained PCR products after separation by agarose gel electrophoresis, but many quantification methods are possible. Technologies not yet fully realized, including NMR or mass spectrometry based methods, may prove useful in the future. However, the current standards are hybridization-based methods. Hybridization-based quantitative methods are very sensitive and can be easily automated with the use of DNA chips or microtitre plate scanners, for example. Incorporation of specific labels is another means of quantification. Product specific primers may be differentially labeled, for example, thus allowing the simultaneous detection of two products. The quantification methods are numerous, and the invention in its broadest form is not limited to a specific methodology in this regard.

The method is exemplified with a continuous flow activated sludge system, but may be employed with any system type, including a sequencing batch test reactor, a packed bed reactor system, an immobilized bacteria system, a fluidized bed reactor system, a trickling filter system, and a rotating biological contactor system, for example.

DESCRIPTION OF EMBODIMENTS OF THE INVENTION

Figure 1:
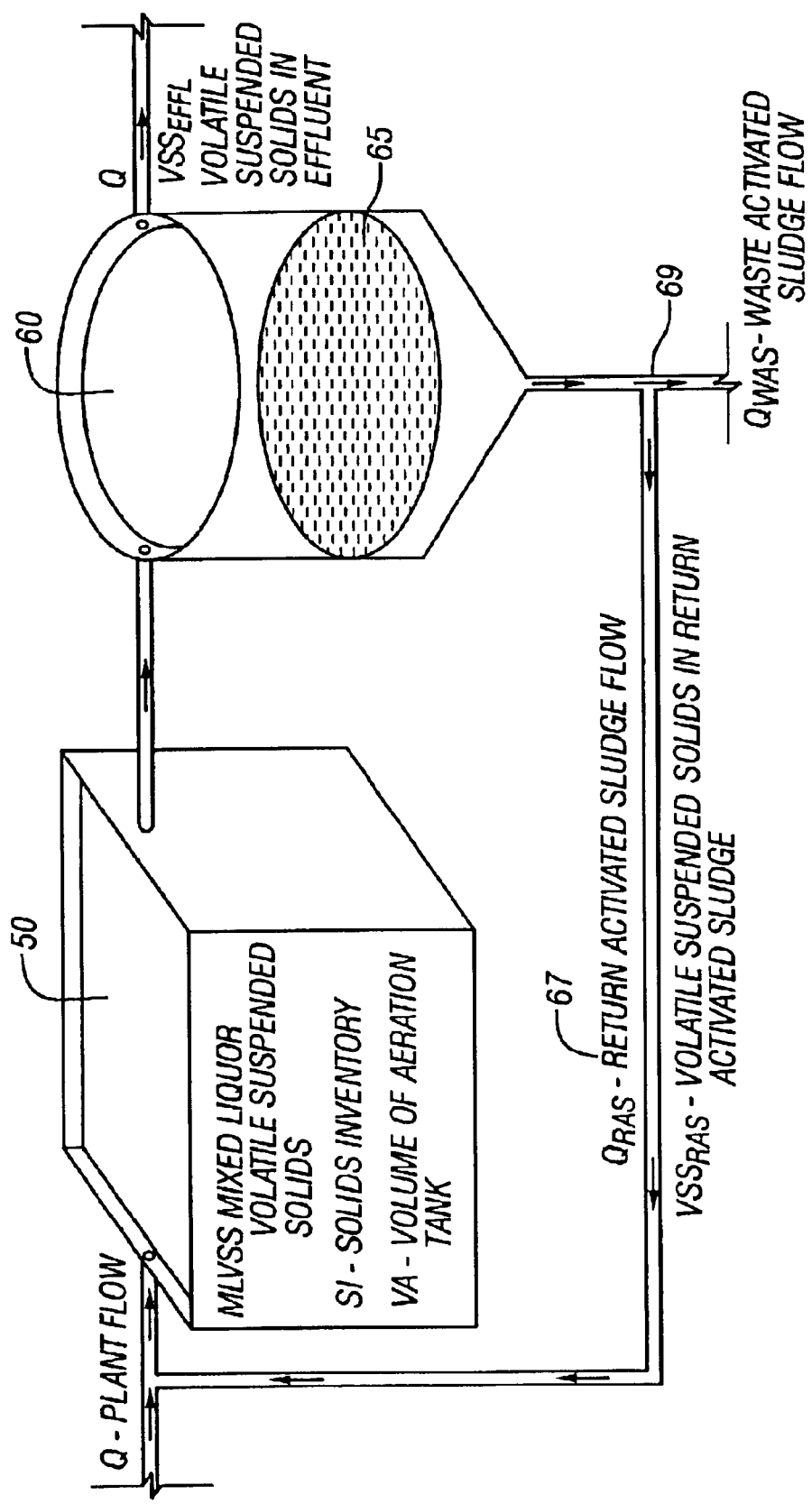
FIG. 1. Typical Components of an Continuous Flow Activated Sludge System.

The present invention is exemplified with respect to the gox gene, but may be performed with any gene important in a biotreatment process, provided only that sequence information about indicator/effector gene combinations be available for use in the generation of specific primers. Ideally, an effector gene codes for a rate limiting enyzme in a given degradative or bioremedial pathway, and the indicator gene is unique to those microbes that employ this pathway. Thus, gene copy number and expression levels will correlate well with the efficacy of the biotreatment process.

The indicator and effector genes may be the same gene. This simplifies the process and ensures that both measurements correlate with degradative potential of the system. However, in another embodiment, an indicator gene and an effector gene are separate genes. The indicator gene may be closely linked to an effector gene (such as the gox gene), so that indicator and effector genes do not become separated. Alternatively, the indicator may be any single copy gene with unique sequences that must be maintained for viability and thus whose abundance accurately correlates with the abundance of the microbe of interest. The indicator gene may even be a common housekeeping gene, provided that the primers used to amplify the indicator gene are unique to the microbes of interest. In this way, gene abundance accurately indicates abundance of the microbe with degradative potential, and other microbes are not quantified. If desired, total microbial content (TMC) can also be measured by analyzing the level of a ubiquitous gene.

Although the system is exemplified herein by reference to the gox gene, many other genes may be employed. For example, microorganisms have been used to sequester, precipitate, or alter the oxidation of various heavy metals (Pazirandeh et al., 1998, Appl. Environ. Microbiol. 64: 4068–4072). The efficiency for reclamation of cadmium or mercury could be assessed by measuring the abundance and expression of the uptake genes mntA (Hao et al., 1999, Appl. Environ. Microbiol. 65: 4746–4752) or merP (or merT) (Ravel et al., 2000, J. Bacteriol., 182:2345–2349), respectively. Table 1 lists some of the genes that may be useful in the invention.

TABLE 1

Substrates and Effector Genes

| Substrate | Effector Gene |
|---|---|
| Glyphosate (N-phosphonomethylglycine) | gox |
| Iminodiacetic acid (IDA) | gox |
| N-phosphonomethyl-iminodiacetic acid (PIA) | gox |
| Naphthalene | nahAc |
| Phenol | poxABCDEF |
| Dehydroabietic acid | ditAl |
| Mercury | merP, merT |
| Cadmium ($Cd^{2+}$) and manganese ($Mn^{2+}$) | mntA |
| Ammonia | amoA |

The invention provides PCR-based methods for accurate, quantitative measurement of both the amount of DNA present for a given indicator gene and levels of expression for the effector gene. Such measurements provide specific information on the amount of specific biotreatment microorganisms present in a given ecosystem (e.g., AMC value as reflected by the level of indicator gene), as well as specific information on the level of biotreatment activity (i.e., ABC value as reflected by the level of expression of effector gene). This information is combined with currently measured waste treatment system parameters to provide not only improved means for monitoring such systems, but also improved methods for active, near real-time control of them.

Application of the invention in the field will typically involve sampling of activated sludges treating glyphosate-containing waste streams and conducting PCR amplification of the indicator/effector gene combinations from the sample. Near real-time control is made possible through information provided by these PCR-based methods. The quantitative measurements of both the abundance of glyphosate-degrading microorganisms and the level of glyphosate degrading activity mediated by gox expression in these microorganisms permit informed changes to be made in control parameters so that more effective wastewater biotreatment, e.g., glyphosate degradation, may be accomplished.

For example, when the indicator gene levels are very low, as reflected by a low active microbe content (AMC), it may be necessary to reseed the sludge with additional microorganisms. When the effector gene expression value is low, as reflected by a low active bioremedial content (ABC), but the AMC indicates that the desired microbes are present, it may be necessary to acclimate the sample before significant loading of the system is begun. When the ABC and AMC are less than optimum, the ABC and AMC measurements can be used to quickly gauge a systems reaction to a given change in parameter, such as change of pH, nitrogen level, loading rates or flow rates. Thus, the ABC and AMC measurements can offer near real-time monitoring of a waste treatment system and thereby offer much quicker optimization of the system.

In one embodiment of the invention, the rate of waste loading increase that may be achieved while avoiding glyphosate breakthrough is determined in an essentially active manner that is specific for the principal mechanism of glyphosate degrading activity (GDA)—gox-mediated catabolism. Glyphosate breakthrough occurs when waste loading exceeds the treatment capacity of a facility's glyphosate treatment system; if glyphosate breakthrough is not observed, loading is somewhere at or below treatment capacity. Conventional approaches (e.g., based on OUR measurements coupled with analyses of key constituents in waste effluent), on the other hand, provide at best passive and nonspecific means for only roughly estimating the rate of waste loading increase that may be achieved while avoiding glyphosate breakthrough.

PCR-based measurements, particularly competitive qPCR and competitive qRT-PCR, provide heretofore unprecedented accuracy in determination of glyphosate waste treatment capacity and specific bioremedial activity. Through use of active microbe content (AMC) determinations in place of crude MLVSS estimates, a precise quantification of gox gene copies, or microbial count, is achieved, thereby providing information that can be used to predict more accurately the degradative capacity of a biotreatment system. Furthermore, through the determination of active bioremedial content (ABC) and specific bioremedial content (SBC) values (SBC=ABC/AMC), direct information on the relative expression or activity of gox gene copies can be obtained for a system. ABC, AMC and SBC values may also be utilized in estimating the capacity of a system to respond rapidly to changing glyphosate loadings.

In one aspect, the invention provides improved methods for determining specific estimates of the microbial biomass that is capable of degrading glyphosate. Conventional methods for determining such estimates rely on measurements of F/M ratios, particularly $F_{BOD}$/M ratios, i.e., BOD (kg/day)/MLVSS (kg). However, processes available for determining estimates of BOD (particularly for glyphosate-specific BOD or $BOD_{gly}$) and MLVSS are generally lengthy and do not permit active, near real-time control of glyphosate degradation.

PCR-based methods provide for measurements of AMC in place of crude MLVSS measurements. AMC estimates that are based on a precise quantification of gox gene copies, i.e., $AMC_{gox}$ estimates, provide information that can be used to predict more accurately the ultimate capacity of a biotreatment system for degrading glyphosate. Furthermore, PCR-based methods also provide for precise, functionally specific measurements of ABC in place of error-prone, non-specific OUR measurements. ABC measurements provide direct information on the expression of the gox gene, i.e., $ABC_{gox}$ measurements, and may further be used to estimate SBC values for gox, i.e., $SBC_{gox}$ values, because $SBC_{gox}$ is the ratio of $ABC_{gox}/AMC_{gox}$. A PCR-based estimate of SBC for a particular effector gene provides a near instantaneous, or quickly-developed, snapshot of a biotreatment system's capacity for degrading a wastewater component.

Methods of the present invention (e.g., for estimating microbial biomass and activity) are quantum improvements over conventional methods for assessing process performance. As noted previously, while conventional methods rely on estimating general and specific F/M ratios as BOD (kg/day)/MLVSS (kg), one aspect of the present invention provides for estimating F/M ratios specific for glyphosate using, in part, PCR-based quantification of the copy number of the indicator gene linked to the effector gene gox. For example, an estimate of a F/M ratio specific for glyphosate would be equal to glyphosate influx (kg/day)/$AMC_{gox}$ (kg), where $AMC_{gox}$ is the mass of live microbes in kilograms that have a copy of the gox effector gene. As another example, a potentially more useful estimate of a F/M ratio specific for glyphosate would be equal to glyphosate influx (kg/day)/$ABC_{gox}$ (kg), where $ABC_{gox}$ is, for this example, the mass of expressed gox mRNA.

As an F/M ratio of conventional methods may be used to relate biotreatment process performance to general waste loading (but only with difficulty for many specific components of wastewater), an F/M ratio as provided by aspects of methods of the present invention may be used to relate biotreatment process performance not only to general waste loading, but also to loading of a specific waste component, such as glyphosate. Conventional methods for determining process parameters cannot provide this information because, inter alia, the estimator of the F/M ratio denominator, i.e., MLVSS, is (a) only a crude measure of biomass and does not distinguish between living or nonliving cells; (b) does not distinguish specific critical components of biomass such as microorganisms that do not carry an effector gene (such as gox) from those that do; and (c) does not provide information on a particular degradative activity, as indicated by mRNA levels.

The F/M ratio of glyphosate influx (kg/day)/$ABC_{gox}$ (kg), does not have the above-noted shortcomings. The denominator $ABC_{gox}$ is based on levels of mRNA expressed by living cells that carry the gox effector gene. Thus, in one aspect the invention provides information for modifying control parameters for efficient GDA in wastewater biotreatment through measurements made possible by PCR-based monitoring.

EXAMPLE 1

PCR-Based Measurements

For analysis of activated sludge, 3.0–4.5 ml samples are obtained as described below and transferred to sterile 1.5 ml microcentrifuge tubes and immediately placed on ice. All subsequent manipulations are done at <4° C. or in the presence of a chaotrophic nucleic acid stabilizing agent (BIO101™, Vista, Calif., now QBIOGENE, Carlsbad, Calif.). A 3.0 ml sample of activated sludge contains approximately 150–200 mg of sludge solids (wet weight). Current estimates of the heterotrophic microbial community indicate that such a 3.0 ml sample contains approximately $2.1 \times 10^8$ bacterial cells. Suspended solids are collected via centrifuge at 15,300 rpm for 30 sec.

Activated sludge mixed liquor is then decanted and sludge pellets are immediately frozen at −80° C. Samples must be stored at −80° C. prior to nucleic acid extraction, unless extraction from sludge pellets proceeds immediately after decanting. Preferably, −80° C. storage should be for a duration of less than 1 week and not longer than 1 month.

Frozen pellets of activated sludge are thawed on ice and resuspended in sterile $H_2O$. Nucleic acids (DNA or RNA) are then promptly extracted using standard kits (e.g. FASTDNA® or FASTRNA® kits (BIO101™), according to manufacturer's recommendations). Extracted DNA is stored at −20° C. Extracted RNA is stored at −80° C. and analyzed within 30 days, although RNA stabilization reagents can prolong RNA shelf life if necessary.

Alternately, RNA can be extracted using a modified hot phenol method (Fleming et al., 1993 Environ. Sci. Technol. 27: 1068–74) in cases where greater quantities of RNA are necessary (e.g., where gox expression levels are low). Extraction of RNA using a modification of this method is as follows: activated sludge pellets are combined with 500 μl lysis buffer (0.05 M sodium acetate (NaAc), 0.05 M NaCl, 0.003 M EDTA, 1.0% SDS, pH 5.2), vortexed well at a medium setting, and incubated at 60° C. for 5 min. 500 μl of acid phenol (NaAc buffered, pH 5.2, prewarmed to 60° C.) and 100 μl chloroform:isoamyl alcohol (24:1) is added and the mixture is vortexed for 10 seconds at a medium setting, and then incubated an additional 5 min at 60° C. The samples are then incubated on ice (4° C.) for 5 min and centrifuged at 15,300 rpm for 15 min.

The supernatants are then transferred to a clean RNAse-free microcentrifuge tube, combined with 1 volume of chloroform:isoamyl alcohol (24:1), vortexed for 10 seconds (medium speed setting), and centrifuged (15,300 rpm) for 5 min. The aqueous phase (top layer) is then transferred to a clean RNAse-free tube, combined with 1/10 volume of 3M NaAc (DEPC-treated) and 1 volume of isopropanol, mixed well by inversion, and incubated at room temperature for 5 min. Following microcentrifugation for 15 min at 15,300 rpm, the supernatant is discarded and the pellet washed with DEPC-treated 70% ethanol. RNA pellets are dissolved in 100 µl DEPC-treated $H_2O$ and stored at −80° C.

Prior to competitive qRT-PCR analysis, contaminating DNA should be removed. RNA samples are combined with 1/10 volume 100 mM $MgCl_2$/10 mM DTT and 100 units of DNAse I (RNAse-free). Samples are mixed well and incubated for 15 min at 37° C. Samples are then mixed again and incubated for an additional 15 min. 1/10 volume of 3M NaAc and 1 volume of isopropanol is then added and sample are incubated for 5 min and centrifuged for 15 min. Pellets are washed 1 time with 70% ethanol (pEPC-treated). RNA template pellets are then dissolved in DEPC-treated $H_2O$ (target concentration 1 µg/µl).

gox primers and various PCR products are presented in Table 2.

TABLE 2A

Sequence Identification

| Name | Sequence | SEQ ID NO |
|---|---|---|
| GA4/GA2 gox PCR product | GCTCGTGACC CTCTTGTTTC GGCGTTTTAT CGCGAACGGT GGCGAATTCG TATCTGCGCG TGTCATCGGC TTTGAGACTG AAGGTAGGGC GCTTAAAGGC ATTACAACCA CGAACGGCGT TCTGGCCGTT GATGCAGCGG TTGTCGCAGC CGGCGCACAC TCGAAATCAC TTGCTAATTC GCTAGGCGAT GA (192) | 1 |
| GA4/GA2 cgox PCR product | GCTCGTGACC CTCTTGTTTC GGCGTTTTAT CGCGAACGGT GGCGAATTCG TATCTGCGCG TGTCATCGGC TTTGAGACTG AAGGTAGGGC GCTTAAAGGC ATTACAACCA CGAACGGCGT TCGCTAATTC GCTAGGCGAT GA (142) | 2 |
| GA1/GA2 gox PCR product | AAGACCAAAC AAGGTGAAGG AGCAGGCGAA AGCACTCCGC AATCTCATCA AGTCCACGGT GCCTCTGATC AAGTCATTGG CGGAGGAGGC TGATGCGAGC CATCTGATCC GCCATGAAGG TCATCTGACC GTATATCGTG GAGAAGCAGA CTTCGCCAAG GACCGCGGAG GTTGGGAACT GCGGCGTCTC AACGGTGTTC GCACGCAGAT CCTCAGCGCC GATGCGTTGC GGGATTTCGA TCCGAACTTG TCGCATGCGT TTACCAAGGG CATTCTTATA GAAGAGAACG GTCACACGAT TAATCCGCAA GGGCTCGTGA CCCTCTTGTT TCGGCGTTTT ATCGCGAACG GTGGCGAATT CGTATCTGCG CGTGTCATCG GCTTTGAGAC TGAAGGTAGG GCGCTTAAAG GCATTACAAC CACGAACGGC GTTCTGGCCG TTGATGCAGC GGTTGTCGCA GCCGGCGCAC ACTCGAAATC ACTTGCTAAT TCGCTAGGCG ATGA (504) | 3 |
| GA1/GA2 cgox PCR product | AAGACCAAAC AAGGTGAAGG AGCAGGCGAA AGCACTCCGC AATCTCATCA AGTCCACGGT GCCTCTGATC AAGTCATTGG CGGAGGAGGC TGATGCGAGC CATCTGATCC GCCATGAAGG TCATCTGACC GTATATCGTG GAGAAGCAGA CTTCGCCAAG GACCGCGGAG GTTGGGAACT GCGGCGTCTC AACGGTGTTC GCACGCAGAT CCTCAGCGCC GATGCGTTGC GGGATTTCGA | 4 |

TABLE 2A-continued

Sequence Identification

| Name | Sequence | SEQ ID NO |
|---|---|---|
| | TCCGAACTTG TCGCATGCGT TTACCAAGGG CATTCTTATA GAAGAGAACG GTCACACGAT TAATCCGCAA GGGCTCGTGA CCCTCTTGTT TCGGCGTTTT ATCGCGAACG GTGGCGAATT CGTATCTGCG CGTGTCATCG GCTTTGAGAC TGAAGGTAGG GCGCTTAAAG GCATTACAAC CACGAACGGC GTTCGCTAAT TCGCTAGGCG ATGA (454) | |

TABLE 2B

Sequence Identification

| Primer | Sequence | SEQ ID NO | Tm °C. | Target site bp |
|---|---|---|---|---|
| GA1 | AAG ACC AAA CAA GGT GAA GGA G | 5 | 48 | gox 300–321 |
| GA2 | TCA TCG CCT AGC GAA TTA GC | 6 | 47 | gox 784–803 |
| GA3 | TCA TCG CCT AGC GAA TTA GCG AAC GCC GTT | 7 | 59 | gox 723–733, 784–803 |
| GA4 | GCT CGT GAC CCT CTT GTT TC | 8 | 49 | gox 612–631 |
| GA2s | TCA TCG | 9 | ND | gox 798–803 |
| T7 | TAA TAC GAC TCA CTA TAG G | 10 | 39 | pCR®II-TOPO 406–425[1] |
| SP6 | CTA TTT AGG TGA CAC TAT AG | 11 | 41 | pCR®II-TOPO 239–256[1] |
| M13r | CAG GAA ACA GCT ATG AC | 12 | 39 | pCR®II-TOPO 205–221[1] |

[1]INVITROGEN Carlsbad, Calif.

Using either the GA1/GA2 primer set or the GA4/GA2 primer set (see U.S. Pat. No. 5,463,175 and U.S. Pat. No. 5,776,760 for additional information on gox PCR), gox PCR products of either 504 bp (SEQ ID NO.: 3) or 192 bp (SEQ ID NO.: 1) in length are generated. A competitor template was also generated using PCR and contains a 50 bp deletion near the 3'-prime end of both the 504 bp and 192 bp gox PCR product. Deletion of 50 bp from the 504 bp gox PCR product to generate the cgox PCR product was facilitated using primer GA3 which targets the 3'-prime end of the gox gene and a region 50 bp upstream of this binding site. Primer binding results in 50 bp of gox DNA being looped away from the primer site and thereby excluded from PCR extension. This yields a 454 bp DNA sequence (SEQ ID NO.: 4); specifically, the 50 bp sequence defined by the thymine residue at position 435 to the thymine residue at position 484 of the 504 bp gox PCR product are deleted. This competitor gox (i.e., cgox) DNA fragment was ligated into a PCR® II-TOPO plasmid vector (INVITROGEN™, Carlsbad, Calif.) containing two promoter sites (T7 and SP6), allowing directional transcription which generates either sense or anti-sense RNA strands.

Routine preparation of cgox mRNA for competitive RT-PCR proceeds as follows: Plasmid DNA is extracted from bacterial hosts (e.g., using Plasmid Midi Kit as per manufacturer's directions (Catalog # 12143, QIAGEN™, Valencia, Calif.)). 5 µg of plasmid DNA is cut using EcoRV and BspHI restriction endonucleases, and digestions are electrophoresed using 1.0% low melting point agarose. Next, the 1654 bp EcoRV-BspHI fragment containing the cgox DNA fragment is then excised from the gel and purified (e.g., using the gel extraction kit by QIAGEN™). Purified DNA is then quantified and subsequently transcribed (e.g., MEGAscript™ In-Vitro Transcription Kit by AMBION™, Austin Tex.). Transcription initiation from the SP6 promoter yields sense strand cgox mRNA. cgox mRNA is then DNAse treated and purified using acidic phenol and chloroform, is quantified and stored at −80° C. until use.

0.1–5.0 µg of DNA-free RNA template is combined with 25.2 pmoles of antisense primer (GA2S or GA2) and 0.01–25 pg cgox mRNA before adjusting the reaction volume to 9.5 µl using sterile DEPC-treated water in a 0.2 ml PCR tube. This primer/template mixture is heated for 5 min at 70° C. and snap cooled to 4° C. (reaction mixtures are maintained at 4° C. prior to the reverse transcription incubation). To this mixture is added 5.5 µl of a master mix containing 200 units MMLV reverse transcriptase/reaction, 1× MMLV reverse transcriptase reaction buffer (e.g., catalog #M1701, PROMEGA™, Madison Wis.), and 1.0 µl 10 mM dNTP mix (ROCHE™, Indianapolis, Ind.). Reverse transcription is allowed to proceed by incubating complete reaction mixtures at 37° C. for 1 hour. A 5 min incubation at 75° C. (in order to inactivate reverse transcription) and a 0–4° C. incubation (for short term storage) follow. DNA mixtures prepared by reverse transcription may kept in long term storage at −20° C.

DNA samples prepared by reverse transcription are subsequently analyzed using the following PCR protocol. Two master mixtures are preferentially used in order to minimize the possibility of generating non-specific amplification artifacts. The first master mixture is the primer mixture, which contains 0.4–1.0 µM of each primer (GA1/GA2 or GA4/GA2), and 0.2 mM of each dNTP; the volume of this primer mixture is adjusted to 24 µl/primer mixture using sterile PCR-grade $H_2O$. The primer mixture is kept chilled at 0–4° C. prior to PCR.

The second master mixture is the Taq enzyme mixture, which contains Taq DNA polymerase (1–5 units/reaction) and 1× PCR buffer (10 mM Tris-HCl, pH 9.0, 50 mM KCl, 0.1% Triton X-100, and 2.0 mM $MgCl_2$); the total volume is adjusted to 24 µl enzyme mixture. The enzyme mixture should also be kept chilled at 0–4° C. prior to PCR. A 2.0 µl aliquot of the cDNA mixture prepared by reverse transcription is then combined with 24 µl primer mixture and 24 µl Taq enzyme mixture in a 0.2 µl PCR tube.

The PCR tubes are maintained at 0–4° C. during mixing and then immediately incubated in a PCR thermocycler according to the following protocol: 1) initial denaturation at 95° C. for 5 min is followed by PCR thermocycling using a denaturation temperature of 92° C. for 15 seconds, annealing at 57.5° C. for 30 seconds, and extension at 72° C. for 30–45 seconds; and 2) after 20–50 cycles of PCR, a prolonged extension at 72° C. for 7 min is executed. Short-term storage of the PCR products is at 4° C.; long term storage is at −20° C.

For DNA analyses, this same PCR protocol, though substituting DNA samples for RNA samples, is used with the following modifications: 1) template concentration is adjusted depending on both the number of cycles desired and the origin of the DNA (e.g., template concentration for chromosomal DNA should be between 0.1–1 µg; and 2) total volume of each PCR reaction is 50 µl.

Quantification of PCR products is performed by agarose gel electrophoresis, although any other method may be used, including hybridization-based methods, such as DNA chip quantification. PCR reactions are combined with 5.5 µl loading dye (e.g., Native Agarose 10× gel loading dye diluted 1:10 with a 40% sucrose solution, AMBION™). 50 µl of this mixture is loaded onto a 1.2–2.5% agarose gel containing 0.4 µg/ml ethidium bromide. Electrophoresis at 80–140 volts for 2–4 hours follows.

Gels are visualized using a gel documentation system (e.g., ALPHAIMAGERTM2200™, by ALPHA INNOTECH CORP.™, San Leandro Calif.) and DNA quantities are determined using densitometry (e.g., as described by ALPHA INNOTECH CORPORATION™).

Alternately and preferably, real-time PCR monitoring is utilized to visualize PCR products. The gox/cgox competitive PCR and RT-PCR strategy is best suited for real-time PCR monitoring using a PCR thermocycler capable of quantification of multiplex PCR products. This could be accomplished in commercially available instruments such as the ICYCLER IQ™ by BIORAD™ (Hercules, Calif.), the MX4000™ by STRATAGENE™ (La Jolla, Calif.), or the LIGHTCYCLER™ by ROCHE™.

The real-time PCR approach could make use of the 50 bp deletion intrinsic to cgox product as a mechanism to differentiate between the gox and cgox products. In theory a probe which targeted the region of the 50 bp deleted region could be used to detect the gox product (using one fluorescence wavelength, such as red) and a second probe could be used for detecting all of the cgox and gox products by targeting another shared region (using a second fluorescence signal, blue). Alternatively, as per the LIGHTCYCLER™, the amplification reaction could be monitored using a non-specific double stranded DNA binding dye such as SYBR GREEN I™ (ROCHE™), coupled with differentiation of the cgox and gox PCR products based on their specific melting temperatures.

These approaches would reduce analysis time by significantly because they eliminate the need for separation of amplification products by electrophoresis and subsequent quantification by densitometry. Real-time PCR would correct completely for heteroduplex formation, would allow failed experiments to be identified immediately, and would allow for enhanced sensitivity by establishing the exact point at which artifacts begin to accumulate.

EXAMPLE 2

Enhanced RNA Extractions on Fayetteville Activated Sludge

RNA extractions were performed using a hot phenol method, as detailed in Example 1, on Fayetteville activated sludge received from the Monsanto manufacturing facility in Fayetteville, N.C. (i.e., Cedar Creek Road, Fayetteville, N.C. 28301). Nucleic acid recovery was increased using the hot phenol method of RNA extraction relative to the FASTRNA™ method. Typically, the hot phenol method of RNA extraction yielded approximately 20 µg DNA-free RNA per 4.5 ml activated sludge. The hot phenol method can also be scaled up to allow greater quantities of RNA to be extracted from activated sludge solids and thereby increase overall yields even further. However, for convenience in implementation, the FASTRNA™ method remains attractive for routine RNA extractions, particularly in contexts where sufficient RNA yields are routinely obtained.

EXAMPLE 3

Enhanced Competitive Quantitative RT-PCR for GOX

Several additional enhancements may be realized in the competitive qRT-PCR procedure. These include enhancing the stability of stock solutions containing gox or cgox mRNA standards (e.g., using 1.0 mM sodium citrate), decreasing detection limits for gox or cgox mRNA, and increasing reverse transcription/replication fidelity in PCR steps of the competitive qRT-PCR procedure for gox.

Competitor gox internal standard gradients were prepared using 10 mM Tris buffered $H_2O$ (for cgox DNA standards) and 1.0 mM sodium citrate (for cgox RNA standards). For cgox DNA, standard solutions containing from 25 pg to 0.1 pg cgox-plasmid vector DNA (e.g., 25, 12.5, 6.25, 3.13, 1.56, 0.78, 0.39, 0.2, and 0.1 pg, i.e., respectively, 2.87, 1.44, 0.72, 0.36, 0.18, 0.09, 0.04, 0.02, and 0.01 pg of actual cgox sequence DNA, where the mass of actual cgox sequence DNA equals vector DNA mass times the ratio of gox insert size to total vector length) per 100 μl mM Tris-buffered $H_2O$ are routinely prepared. For cgox RNA standards, solutions containing 10 to 0.01 pg cgox RNA (e.g., 10, 5, 2.5, 1.25, 0.63, 0.31, 0.16, 0.08, 0.04, 0.02, and 0.01 pg) per approximately 100 μl 1.0 mM sodium citrate are routinely prepared.

Extensive DNAse treatment of RNA prior to RT-PCR is important and is completed as detailed in Example 1. Experiments on specific reverse transcription protocols suggests that RNA secondary structure can dramatically affect experimental results. By inclusion of a preliminary denaturation step, a linear increase in gox cDNA production has been observed when using between 0.5 to 5.0 μg total RNA isolated from Fayetteville activated sludge. The combined use of increased RNA loading and buffered mRNA standards for these studies has allowed detection of as little as about 9.08 μg gox mRNA (i.e., $1\times10^{-15}$ g gox mRNA) per 1.0 to 5.0 μg total RNA.

Figure 3:
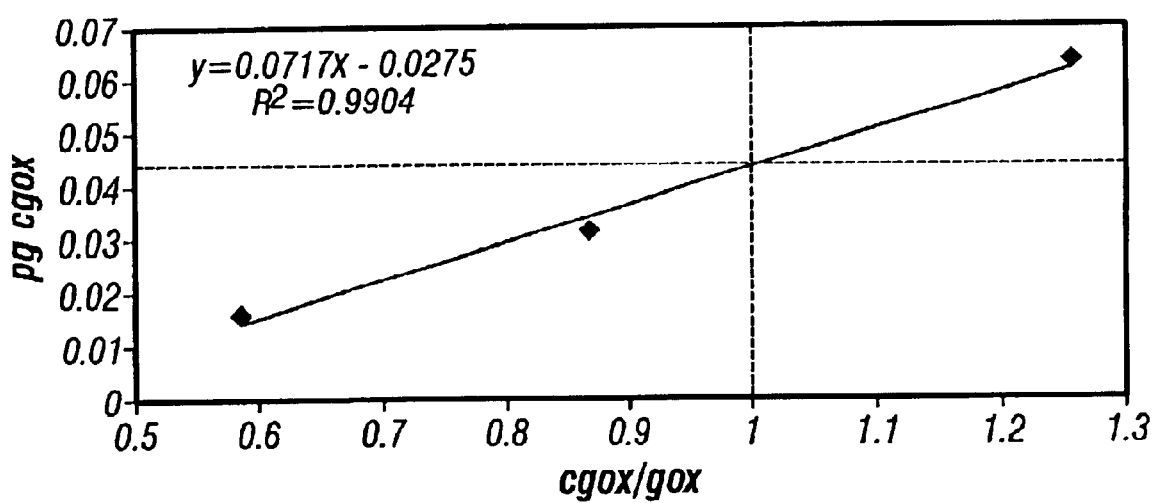
FIG. 3. Quantification of gox mRNA for Reactor A. Following electrophoretic separation of gox and cgox PCR products and densitometric quantification, the ratios of cgox PCR products and gox PCR products for each internal standard concentration were plotted against the known value of cgox (pg) added to each reaction. The data is analyzed using linear regression analysis. The point at which the ratio of cgox:gox equals 1 represents the point of equivalency.
Figure 4:
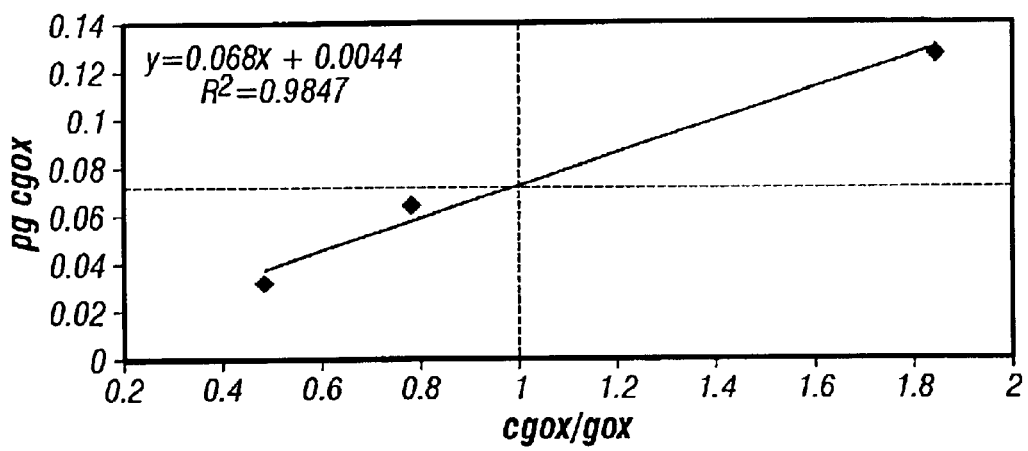
FIG. 4. Quantification of gox mRNA for Reactor B. See FIG. 3 for details.

Results from gox competitive qRT-PCR experiments demonstrated linear amplification for cgox mRNA, as determined by quantification of cgox and gox product following electrophoretic separation in 2.0% agarose gels. Negative control lanes (i.e., RNA samples prepared without a reverse transcription step) were without bands after such electrophoresis. Regression analyses on densitometry measurements demonstrated that the data fit within acceptable limits a linear model as shown in FIGS. 3 and 4.

In particular, after densitometric measurement of PCR product levels, the concentration of cgox in Reactor A (referring to FIG. 3) was calculated to be $3.77\times10^4$ copies of gox mRNA/μg total RNA, as follows:

y=mx+b, where m=slope and b=y intercept y=0.0717x−0.0275 (by linear regression analysis on three data points)

y=0.0442 pg of cgox=0.0442 pg of gox when x=1, i.e., where cgox/gox=1 but 5.0 μg total RNA was used, so 0.0442 pg cgox÷5.0 μg total RNA=0.0088 pg cgox/μg total RNA 0.0088 pg cgox/μg total RNA×4280249 copies cgox/pg cgox=$3.77\times10^4$ copies of cgox/μg total RNA starting material. Thus there are also $3.77\times10^4$ copies of gox RNA/μg total RNA starting material.

Similarly, after densitometric measurement of PCR product levels, the concentration of cgox in Reactor B (referring to FIG. 4) was calculated to be $1.24\times10^5$ copies of gox mRNA/μg total RNA as follows:

y=mx+b, where m=slope and b=y intercept y=0.068x+0.0044 (by linear regression analysis on three data points)

y=0.0724 pg of cgox=0.00724 pg of gox when x=1, i.e., where cgox/gox=1 but 2.5 μg total RNA was used, so 0.0724 pg cgox÷2.5 μg total RNA=0.0290 pg cgox/μg total RNA 0.0290 pg cgox/μg total RNA×4280249 copies cgox/pg cgox=$1.24\times10^5$ copies of cgox/μg total RNA starting material. Thus there are also $1.24\times10^5$ copies of gox RNA/μg total RNA starting material.

Integrated optical densities (IODs) for cgox and gox, which were used to generate the three data points of FIG. 3 and FIG. 4, are provided in Table 3.

TABLE 3

Integrated Optical Densities (IOD) for GOX RNA Copy Number Estimates

| Reactor | cgox (pg) | gox IOD | cgox IOD | cgox IOD/gox IOD |
|---|---|---|---|---|
| A | 0.127608 | 39198.7776 | 113520 | |
| A | 0.063804 | 102257.6808 | 128656 | 1.2582 |
| A | 0.031902 | 54537.4298 | 47300 | 0.8673 |
| A | 0.015951 | 64763.1978 | 37840 | 0.5843 |
| A | 0.008016 | 66467.4925 | 34056 | |
| B | 0.511250 | 20721.7732 | 172530 | |
| B | 0.255625 | 24175.4020 | 99684 | |
| B | 0.127608 | 39716.7319 | 72846 | 1.8341 |
| B | 0.063804 | 51804.4329 | 40257 | 0.7771 |
| B | 0.031902 | 51804.4329 | 24921 | 0.4811 |
| B | 0.015951 | 24175.4020 | 11502 | |
| B | 0.008016 | 62165.3195 | 11502 | |

The preceding examples describe gox mRNA quantification. In order to quantify gox DNA, the same procedure is used except that instead of using 5.0 μg total RNA (as for Reactor A) or 2.5 μg total RNA (as for Reactor B), only 0.1 μg total DNA was used. Therefore, the pg cgox DNA value is divided by 0.1 μg total DNA. Furthermore, that quotient is multiplied by the conversion factor of 2140125 copies of cgox DNA/pg cgox.

EXAMPLE 4

Waste Treatment Simulation

Figure 2:
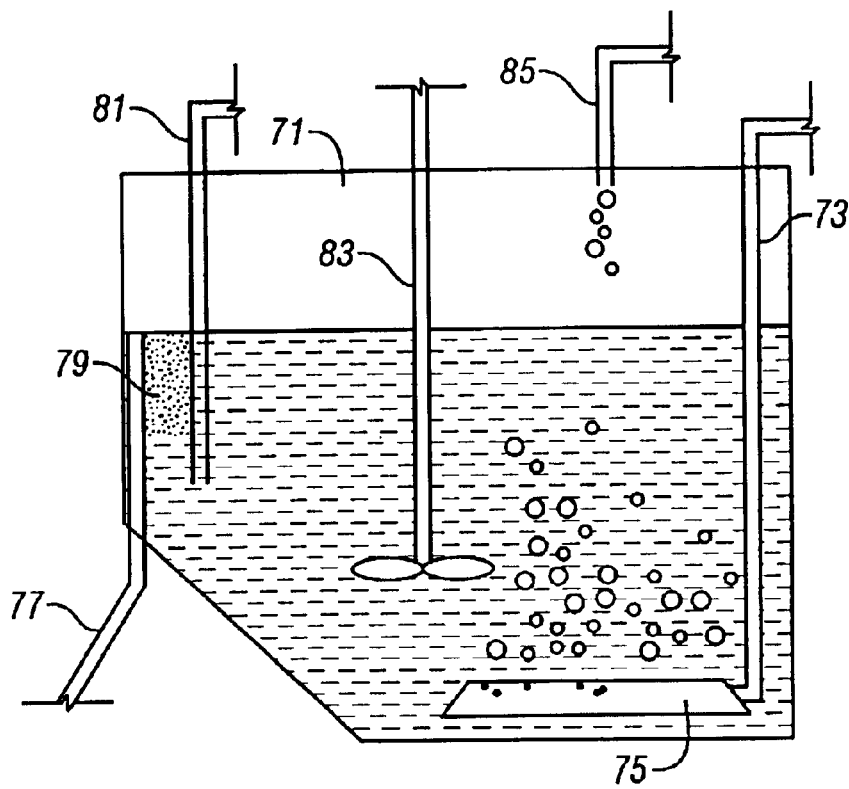
FIG. 2. Single Stage Test Reactor.

Two continuous flow reactors of the Eckenfelder design (Adams, C. E., D. L. Ford, and W. W. Eckenfelder, 1981, *Development of Design and Operational Criteria for Wastewater Treatment*. Enviro Press Inc., Nashville, Tenn.) were used in these studies. FIG. 2 shows a general design for a single stage test reactor. The waste fluid tank (or reactor) 71 is mixed with mixer 83. House air is provided through air tube 73 and dispersed via air stone 75. If necessary, a baffle 81 is included to allow solids to settle near the weir 79 before fluid is removed via waste effluent tube 77. Feed is provided to the tank 71 by feed tube 85.

Experiments were performed to determine the optimal operating parameters for degradation of glyphosate in the two above reactors. Mixing the reactors was done by use of an electric laboratory mixer and an aquarium type air stone. Mixed sludge overflowed the weir into a clarifier placed below the bench. Effluent flowed from the clarifier (by gravity) into a waste container and the settled sludge was pumped back up into the reactors using an adjustable rate peristaltic pump (MASTERFLEX™, COLE-PARMER INSTRUMENT CO.™, Chicago Ill.) hooked to an interval timer (CONTROL™, LINDBURG ENTERPRISES, INC.™, San Diego Calif.). House air (with emergency switching system to tank air) was pumped through flasks of distilled water for humidifying purposes before being pumped into the reactors. Dissolved oxygen levels in the reactors were maintained between 2.0 and 4.0 mg/L. Aquarium heaters were used with electrical controllers to maintain the temperature of the mixed liquor between 19 and 23° C.

Each reactor was seeded with 2.2 L activated sludge received from the Monsanto manufacturing facility in Fayetteville, N.C. Authentic influent wastewater from the Fayetteville facility was used as feed for the laboratory biological reactors and was stored in a cold room maintained at 4° C. prior to use.

The influent pH of the reactors was adjusted with 96.2% $H_2SO_4$ in order to maintain a mixed liquor pH of 6.8 to 7.8. A solution of $NH_4OH$ was added to supplement the reactor feed with an additional 15–30 mg/L $NH_4^+$. Influent wastewater was supplied to the reactors using peristaltic pumps (COLE-PALMER INSTRUMENT CO.™, Chicago, Ill.) at a hydraulic flow rate adequate to produce a reactor HRT of 3.3 days. Tap water was continuously added to reactors, also using peristaltic pumps, to compensate for evaporative losses. Volumes of mixed liquor were regularly removed from the reactor to maintain MLVSS values at 4000 to 5000 mg/L and average sludge age values at 60 to 100 days. A $F_{BOD}/M$ ratio between 0.14–0.25 days$^{-1}$ was maintained to provide a consistent level of glyphosate degradation in the reactors.

These tests showed that optimal parameters for glyphosate degradation were a MCRT of 40 to 80 days, HRT of 3 to 6 days, MLVSS of 4 to 8 g/L, influent BOD of 3500 to 6000 mg/L, $F_{BOD}/M$ of 0.14 to 0.23 days$^{-1}$, temperature of 18 to 35° C., influent nitrogen concentration of 10 to 30 mg/L, and influent phosphate concentration of 50 to 250 mg/L.

The same system is tested with the above described PCR methods described in Example 1. The levels of product produced by competitive qPCR and competitive qRT-PCR are measured at the optimal operating parameters as described above, and the system is perturbed in various respects in order to observe the change in PCR products. A number of parameters are determined, including:

Active microbe content (AMC) is the competitive qPCR product amount×$CF_1$, where $CF_1$ is a first conversion factor. Active bioremedial content (ABC) is the competitive qRT-PCR product amount×$CF_2$, where $CF_2$ is a second conversion factor. Specific bioremedial content (SBC) is ABC/AMC×$CF_3$. The conversion factors may be 1 or may be of any units convenient to the operator.

The experimental design used for changing the glyphosate loading to laboratory reactors is depicted in Table 4.

TABLE 4

Glyphosphate Loading Studies Using Laboratory Reactors

| Loading Phase Number | Influent Glyphosate Conc. (mg/L) Reactor A | Influent Glyphosate Conc. (mg/L) Reactor B |
|---|---|---|
| 1 | 140 | 600 |
| 2 | 300 | 1000 |
| 3 | 1000 | 1000 |
| 4 | 1000 | 300 |

Table 5 provides an example, detailing gox DNA and gox mRNA yields before and after glyphosate loading to two reactors.

TABLE 5

GOX DNA and MRNA Yields before and after Glyphosate Loading

| | Reactor A | | Reactor B | |
|---|---|---|---|---|
| | Before loading | After loading | Before loading | After loading |
| Glyphosate Loading (mg/L) | 140 | 300 | 600 | 1000 |
| AMC = fg gox DNA/$\mu$g total DNA | 379 | 594 | 1620 | 5790 |
| ABC = fg gox mRNA/$\mu$g total RNA | * | 3.7 | ** | 18.4 |
| SBC = ABC/AMC × 1000 | NA | 6.2 | NA | 3.2 |

*at or below detection limit,
**detected, but not quantified

In Table 5, AMC is arbitrarily chosen to be expressed in units of fg of PCR product per $\mu$g of starting DNA extracted from a particular sample, rather than the mass (kg) of gox gene-containing biomass per $\mu$g of starting DNA. Thus, the measurement assumes that DNA extraction efficiencies are equivalent for different samples, and that sample treatment is otherwise consistent. Experiments are planned to confirm that extraction efficiencies are consistent, and if significant variation is observed, nucleic acid spiking studies may be performed to normalize the data or extraction and/or reverse transcription methodologies optimized for consistency of results.

Similarly, ABC in Table 5 is arbitrarily chosen to be expressed in units of fg of gox mRNA per $\mu$g of starting RNA used for qRT-PCR. In this case, total RNA was used, but if sensitivity is an issue, polyA$^+$ RNA could be used for eukaryotic biotreatment organisms. In either case, experiments should be employed to ensure that extraction efficiencies, reverse transcription, amplification, and, if used, polyA$^+$ selection efficiencies are not a source of significant variation in RT-PCR methods. One way to ensure extraction consistency is to quick freeze the sample pellet in liquid nitrogen, and to thaw the sample in phenol, thus preventing the possibility of RNAse activity after harvest. Of course, many methods of reliably extracting and handling RNA are available, and it is assumed that the practitioner is sufficiently skilled in this regard.

Table 6 provides an additional example of the reproducible response of the measured PCR products to the glyphosate loading under steady state conditions. The experiments were performed on 3 or 4 different days, using real effluent which can vary in content.

TABLE 6

GOX DNA and mRNA levels during Glyphosate Loading Phases 3 and 4

| Gox DNA fg gox DNA/ug total DNA | | | | Gox mRNA fg gox RNA/ug total RNA | | | |
|---|---|---|---|---|---|---|---|
| Reactor A | Loading mg/L | Reactor B | Loading mg/L | Reactor A | Loading mg/L | Reactor B | Loading mg/L |
| 17,300 | 1000 | 13,600 | 1000 | 0.93 | 1000 | 1.42 | 1000 |
| 13,600 | 1000 | 12,700 | 1000 | 1.82 | 1000 | 1.78 | 1000 |
| 13,900 | 1000 | 11,100 | 1000 | 1.91 | 1000 | 1.42 | 1000 |
| 11,200 | 1000 | 5,200 | 300 | 4.08 | 1000 | 0.91 | 300 |
| 9,700 | 1000 | 4,800 | 300 | 5.09 | 1000 | ND | 300 |
| 10,500 | 1000 | 5,100 | 300 | 4.49 | 1000 | 0.15 | 300 |
| 12,000 | 1000 | 5,000 | 300 | 5.9 | 1000 | 1.01 | 300 |

*ND = not detected

In this example, under equivalent glyphosate loading conditions measured levels of of gox DNA and mRNA are similar. In contrast, the abundance of both gox DNA and mRNA PCR products decreased in Reactor B as the influent glyphosate concentration was reduced from 1000 to 300 mg/L.

Thus, the examples illustrate that gox DNA and mRNA levels correlate with glyphosate-degrading activity. The production of gox PCR products was enhanced as glyphosate loading to reactors was increased (Table 5). Further, the level of gox PCR products declined as the loading of glyphosate to a laboratory reactor was reduced (Table 6, Reactor B).

Figure 5:
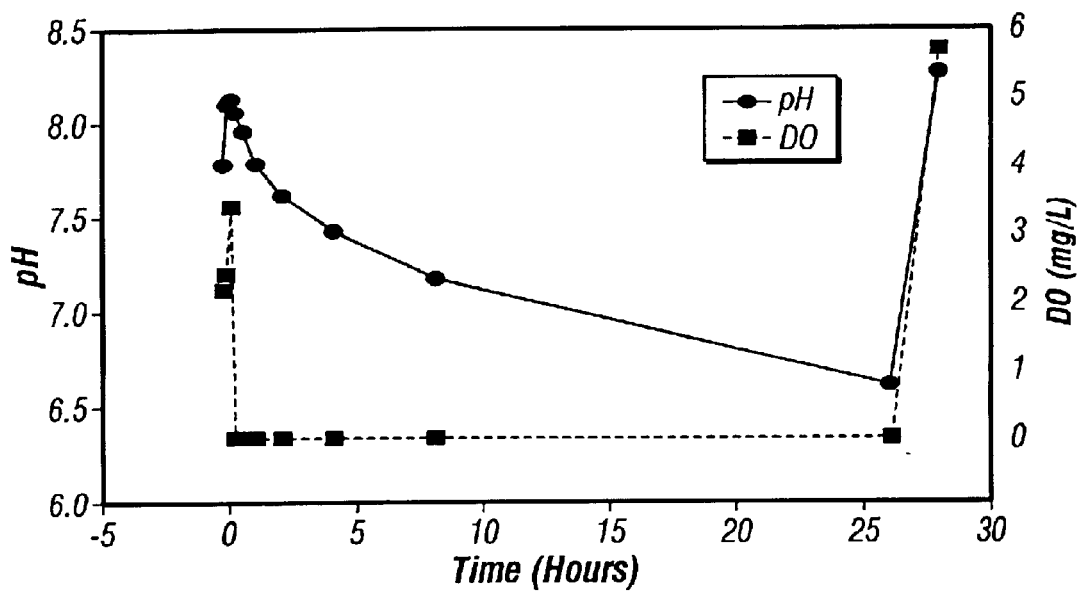
FIG. 5. Reactor Dissolved Oxygen (DO) Perturbation Experiment

An experiment was performed to determine gox DNA and mRNA levels in response to a simulated system perturbation or process upset condition of zero mg/L dissolved oxygen (DO). Using a continuous flow laboratory reactor, the DO concentration was reduced from 4–5 to 0 mg/L, held at 0 mg/L for a 24-hr period, and then returned to normal operating conditions of 4–5 mg/L (See FIG. 5). In response to the system perturbation, the pH of the reactor mixed liquor decreased from 8.0–8.3 to 6.7, consistent with reduced biological activity of the activated sludge microorganisms.

Figure 6:
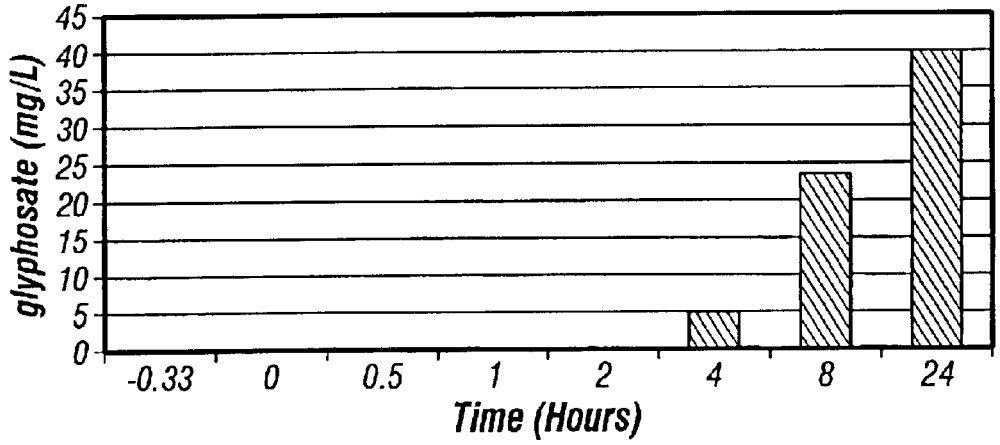
FIG. 6. Glyphosate Breakthrough during DO Perturbation Experiment
Figure 7:
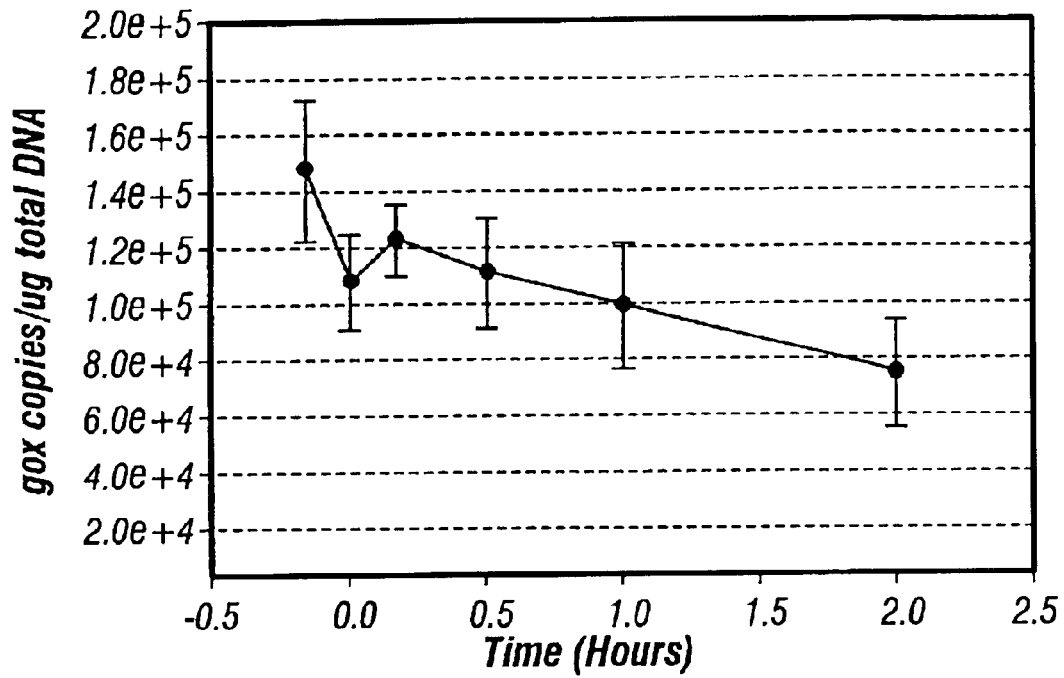
FIG. 7. Glyphosate DNA during DO Perturbation Experiment
Figure 8:
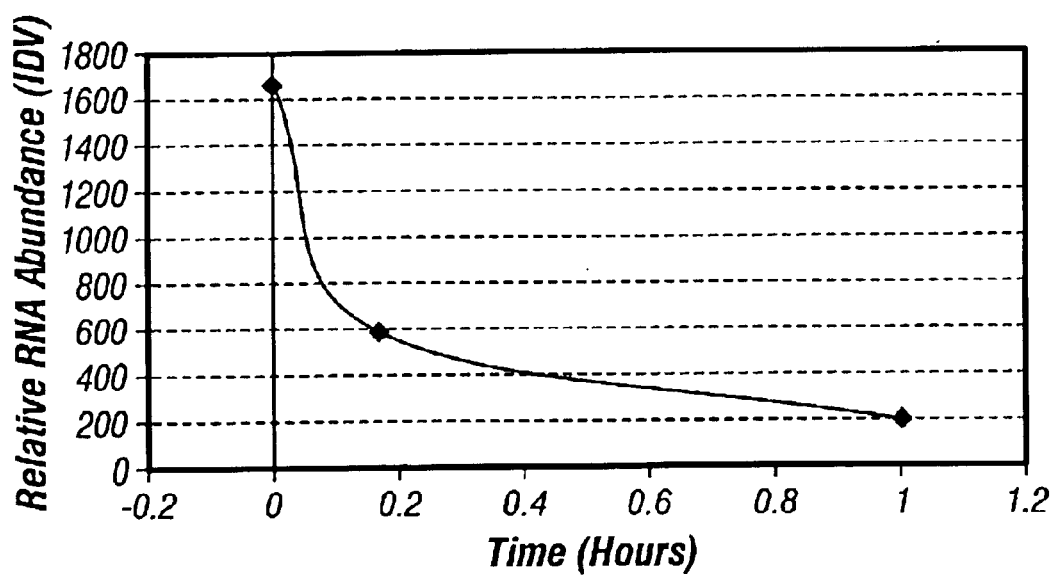
FIG. 8. Glyphosate RNA during DO Perturbation Experiment

In the same experiment, glyphosate was initially detected in the reactor after 4 h and reached levels of 40 mg/L after 24 h (FIG. 6). These results are consistent with the finding that oxygen is utilized by the GOX enzyme in the conversion of glyphosate to AMPA (U.S. Pat. No. 5,463,175). While gox DNA abundance decreased slowly during the first 2 h of the experiment (FIG. 7), gox mRNA abundance decreased rapidly; about a 66% reduction within 10 min (FIG. 8).

The data is supportive that rapid changes in glyphosate degrading activity are mediated through control of gox mRNA production or the ABC, and that the PCR-based monitoring approach can quickly detect changes in biological treatment efficiency. In a 3–6 hr turnaround time, a quantitative assessment of the size of the microbial population responsible for GDA is provided through the determination of the abundance of gox DNA, which can be thought of as measuring glyphosate-degrading potential. In tandem, a quantitative assessment of levels of gox gene expression is provided through the determination of gox mRNA levels, which represents GDA as expressed by the microbial population responsible for GDA at the point in time of sampling. Such data can be used to correlate given gox DNA and RNA levels with a given glyphosate treatment capacity. Outputs generated in this embodiment of the invention, i.e., gox DNA abundance and gox mRNA expression levels, provide an active, rather than passive, means for process control of a glyphosate biotreatment system. Such data are predictive of a system's biotreatment capacity for glyphosate in this embodiment of the invention, or for other specific target constituents of biotreatment facilities in other embodiments

EXAMPLE 5

Monitoring PIA Degradation gox DNA was strongly detected in a reactor seeded with activated sludge treating wastewater containing N-phosphonomethyliminodi-acetic acid (PIA), another substrate for the gox protein. However, gox DNA was not detected in a control reactor that lacked PIA. Accordingly, these results indicate that PCR-based monitoring according to aspects of the present invention may be used to monitor not only glyphosate degradation, but also PIA degradation.

EXAMPLE 6

Determining the Effect of Nitrogen/Micro Nutrients on GDA

Previous studies have shown that addition of ammonia may improve the treatment efficiency of glyphosate in biological treatment systems (Hallas et al. 1992. Appl. Environ. Microbiol. 58: 1215–1219; Heitkamp et al. 1992. Can. J. Microbiol. 38: 921–928). However, until now there has been no method available for specifically determining the effect of nitrogen on GDA, and the observed increase may have been due to either indirect effects of promoting bacterial nitrification or directly increasing the number and/or activity of glyphosate-degrading bacteria. There has also been no method available for specifically determining the effect of the addition of micro nutrients, with or without nitrogen (e.g., in the form of ammonia), on GDA.

The invention as applied in the manner described in Example 4 (i.e., providing measurement of both the abundance and activity of microbes containing effector genes such as gox) would show quantitatively any effect of ammonia on the size and/or activity of the functional glyphosate-degrading population rather than on the general activated sludge microbial community. Existing conventional approaches cannot provide such detailed information and, therefore, such approaches do not permit as effective modifications of control processes.

The invention as applied in the manner described in Example 4 would also show quantitatively any effect of the addition of micro nutrients on the size and/or activity of the functional glyphosate-degrading population. In the case of micro nutrient addition, however, the effect of micro nutrient addition on gox AMC and/or ABC may initially assessed in the laboratory using a yeast extract as the micro nutrient supplement—yeast extract is a common source of vitamins and trace nutrients. If beneficial, subsequent experiments are conducted to assess the effectiveness of adding commercially-available micro nutrient formulations to large-scale biological treatment systems.

EXAMPLE 7

Effect of Toxic Molecules (or any Inhibitory Factor) on GDA

Similarly, the invention provides for methods that can be used to test the effect of a toxic substance (or any inhibitory factor) on GDA and determine if toxicity (or inhibition) is due to cell lethality or due to general effects on gene expression. Toxic substances might include any of a number of cell-killing compounds, including cyanide. Inhibitory factors might include excursions in, for example, pH, temperature, dissolved oxygen, ionic strength, or any key parameter for activated sludge outside of design operational limits. A control housekeeping gene can be monitored in addition to an effector gene in order to provide a control for evaluating cell health. Use of the invention in this case would provide detailed information on whether the toxic event killed cells, generally effected cell health or specifically effected expression of genes in the GDA pathways.

Output obtained according to this embodiment of the invention would help to define the required corrective action, such as resuscitating bacteria necessary for GDA activity that are already present in a system or seeding into a system additional amounts of such bacteria.

EXAMPLE 8

Monitoring GDA in a Continuous Flow System

Several traditional approaches to identifying conditions conducive to the establishment and maintenance of acclimated glyphosate oxidizers in activated sludge have been implemented in the past. PCR-based monitoring carried out according to one aspect of the present invention would greatly enhance the efficiency of these approaches.

Activated sludge processes have played a key role in the biotreatment of glyphosate process wastes. Different microbial populations have been found in activated sludge used to treat glyphosate process wastewater versus those found in domestic activated sludge. Industrial isolates have been found to be capable of utilizing a wider range of organic material (including glyphosate), which has suggested a more diverse microbial taxonomy.

Approaches in field studies to establishing GDA in activated sludge of wastewater biotreatment systems have included: (1) seeding with sludge from an industrial biosystem aerobic digester, (2) seeding with process waste stream containing high levels of glyphosate, and (3) combining concentrated feed amendments with an increased HRT (i.e., for a lower F/M ratio). Such field studies have been hobbled in part by necessary delays between sampling and measurement determinations, as well as by inadequate information for making effective changes in control processes (e.g., by adjusting MCRT, HRT, MLVSS, microorganism community structure, temperature, pH, dissolved oxygen, salt concentration (e.g., phosphates, sulfates, or nitrates), and/or organic compound concentration in activated sludge).

PCR-based monitoring carried out according to one aspect of the present invention would greatly enhance the efficiency of all of these approaches, particularly through implementation of control processes carried out according to another aspect of the present invention. For example, PCR-based monitoring may be used to assess the treatment capacity of glyphosate-laden waste streams prior to observing glyphosate in the effluent. Glyphosate-laden waste streams at high loading levels are often inhibitory to microbial activities required for COD, BOD, or glyphosate removal. Determinations of gox abundance and expression levels can be predictive of an imminent loss in GDA required for treating high loading levels of glyphosate. In some biotreatment systems, the ratio of gox mRNA transcript levels to gox DNA sequences present (as represented by the gox SBC value) is reduced before glyphosate can be measured in the final effluent. With precise knowledge of the relationship over time between gox SBC values and glyphosate amounts likely to appear in the final effluent, informed and effective adjustments could be made to key control parameters (e.g., glyphosate loading rate could be decreased by lowering the influent hydraulic loading rate, in order to increase the hydraulic retention time) so that longer reaction times could be made available to microbes present in the activated sludge for the degradation of glyphosate.

EXAMPLE 9

Monitoring GDA in a Sequencing Batch Reactor

Semicontinuous waste treatment operations, such as those utilizing sequencing batch reactors, are a time-oriented processes that may take place in a single tank. In many cases, utilizing sequencing batch reactors offer distinct advantages over traditional activated sludge processes for secondary treatment designs. For example, operational strategies that provide strong selective pressures can be more easily implemented in such systems; only a single tank (or tank sequence) need be used in a regime of FILL, REACT, SETTLE, DRAW, and IDLE processes. PCR-based monitoring would greatly enhance the efficiency of this approach, particularly through the real-time monitoring and system optimization that PCR-based methods make possible.

EXAMPLE 10

Monitoring GDA in an Immobilized Cell System

One particularly attractive application of immobilized bacteria technologies is for the "polishing" or "final removal" of low concentrations of specific chemicals from high volume liquid waste streams. In particular, bacteria immobilized in a packed bed reactor have been shown to be highly effective for the tertiary removal of low levels of active herbicide from wastewater prior to discharge. As was the case for continuous flow and utilizing sequencing batch reactor activated sludge processes, however, PCR-based monitoring would greatly enhance the efficiency of immobilized bacteria systems.

All references and patents cited herein are expressly incorporated in their entirety by reference.

What is claimed is:

1. A method of optimizing a waste treatment system, the method comprising:
   a. sampling wastewater from a waste treatment system;
   b. collecting solids from said sample;
   c. isolating DNA from said solids;
   d. isolating RNA from said solids;
   e. performing quantitative PCR (qPCR) on said DNA to determine indicator gene abundance;
   f. performing quantitative RT-PCR (qRT-PCR) on said RNA to determine effector gene expression;
   wherein the indicator gene abundance correlates with the active microbial content (AMC) of said sample,
   wherein the effector gene expression correlates with the active bioremedial content (ABC) of said sample, and
   wherein the system is perturbed and steps a) through f) are repeated until the AMC and ABC are within an empirically determined optimal operating range.

2. A method of optimizing a waste treatment system, the method comprising:
   a. sampling wastewater from a waste treatment system;
   b. collecting solids from said sample;
   c. isolating DNA from said solids;
   d. isolating RNA from said solids;
   e. performing competitive qPCR on said DNA to determine indicator gene abundance;
   f. performing competitive qRT-PCR on said RNA to determine effector gene expression;
   wherein the indicator gene abundance correlates with the active microbial content (AMC) of said sample,
   wherein the effector gene expression correlates with the active bioremedial content (ABC) of said sample, and
   wherein the system is perturbed and steps a) through f) are repeated until the AMC and ABC are within an empirically determined optimal operating range.

3. A method of optimizing a waste treatment system, the method comprising:
   a. sampling wastewater from a waste treatment system;
   b. collecting solids from said sample;
   c. isolating DNA from said solids;
   d. isolating RNA from said solids;
   e. performing competitive qPCR on said DNA to determine gox gene abundance;
   f. performing competitive qRT-PCR on said RNA to determine gox gene expression;
   wherein the gox gene abundance correlates with the active microbial content (AMC) of said sample,
   wherein the gox gene expression correlates with the active bioremedial content (ABC) of said sample, and
   wherein the system is perturbed and steps a) through f) are repeated until the AMC and ABC are within an empirically determined optimal operating range.

4. A method for determining levels of abundance and expression of an indicator/effector gene combination within a biotreatment system, the method comprising:
   a. collecting microorganisms from a microorganism-containing stream of a biotreatment system;
   b. isolating from DNA and mRNA from said microorganisms;
   c. determining levels of indicator gene abundance by qPCR analysis of said DNA;
   d. determining levels of effector gene expression by qRT-PCR analysis of said mRNA;
   wherein said indicator gene is the same as said effector gene or wherein said indicator gene is different from said effector gene.

5. A method for controlling a biotreatment system comprising:
   a. sampling a microorganism-containing stream of said biotreatment system;
   b. collecting microorganisms from said sample;
   c. isolating DNA from said microorganisms;
   d. isolating RNA from said microorganisms;
   e. determining an active microbial content (AMC) value for said sample by qPCR analysis of said DNA;

f. determining an active bioremedial content (ABC) value for said sample by qRT-PCR analysis of said RNA;
g. setting a target AMC value for said sample;
h. setting a target ABC value for said sample;
i. comparing said determined AMC value to said target AMC value;
j. comparing said determined ABC value to said target ABC value; and
k. adjusting control processes so as to make said determined AMC and ABC values closer to said target AMC and ABC values when repeating steps a) through e), i), and j).

6. A method for controlling a biotreatment system comprising:
a. sampling a microorganism-containing stream of a biotreatment system;
b. collecting microorganisms from said sample;
c. isolating DNA from said microorganisms;
d. isolating RNA from said microorganisms;
e. determining a specific bioremedial content (SBC) value for said sample by qPCR analysis of said DNA and qRT-PCR analysis of said RNA;
f. setting a target SBC value for said sample;
g. comparing said determined SBC value to said target SBC value; and
h. adjusting control processes so as to make said determined SBC value closer to said target SBC value when repeating steps a)–e) and g).

7. The method as in any of one of claims 1–6 wherein said effector gene is selected from the group consisting of gox, nahAc, pox, ditAl, merP, merT, amoA and mntA.

8. The method as in any of one of claim 1–6 wherein said effector gene is gox.

9. The method as in any of one of claims 5–6 wherein said adjusting control processes is selected from a group consisting of adjusting mean cell retention time (MCRT), hydraulic retention time (HRT), mixed liquor volatile suspended solids (MLVSS), microorganism community structure, temperature, pH, dissolved oxygen concentration, salt concentration, macro nutrient levels, micro nutrient levels, and organic compound influent rate.

10. The method as in any of one of claims 1–3 wherein said system perturbation is selected from a group consisting of adjusting mean cell retention time (MCRT), hydraulic retention time (HRT), mixed liquor volatile suspended solids (MLVSS), microorganism community structure, temperature, pH, dissolved oxygen concentration, salt concentration, macro nutrient levels, micro nutrient levels, and organic compound influent rate.

11. The method as in any of one of claims 1–3 wherein said waste treatment system is selected from the group consisting of a continuous flow activated sludge system, a sequencing batch reactor system, a packed bed reactor system, an immobilized bacteria system, a fluidized bed reactor system, a trickling filter system, and a rotating biological contactor system.

12. The method as in any of one of claims 4–6 wherein said biotreatment system is selected from the group consisting of a continuous flow activated sludge system, a sequencing batch reactor system, a packed bed reactor system, an immobilized bacteria system, a fluidized bed reactor system, a trickling filter system, and a rotating biological contactor system.

13. The method of claim 1, 4, 5, or 6 wherein said qPCR is competitive, noncompetitive, kinetic, or combinations thereof and wherein said qRT-PCR is competitive, noncompetitive, kinetic, or combinations thereof.

* * * * *

SEQUENCE LISTING

<160> NUMBER OF SEQ ID NOS: 12

<210> SEQ ID NO 1
<211> LENGTH: 192
<212> TYPE: DNA
<213> ORGANISM: OCHROBACTRUM ANTHROPI STRAIN LBAA
<220> FEATURE:
<223> OTHER INFORMATION: GENERATED FROM BACTERIA PCR PRODUCT

<400> SEQUENCE: 1

```
gctcgtgacc ctcttgtttc ggcgttttat cgcgaacggt ggcgaattcg tatctgcgcg      60
tgtcatcggc tttgagactg aaggtagggc gcttaaaggc attacaacca cgaacggcgt     120
tctggccgtt gatgcagcgg ttgtcgcagc cggcgcacac tcgaaatcac ttgctaattc     180
gctaggcgat ga                                                         192
```

<210> SEQ ID NO 2
<211> LENGTH: 142
<212> TYPE: DNA
<213> ORGANISM: OCHROBACTRUM ANTHROPI STRAIN LBAA
<220> FEATURE:
<223> OTHER INFORMATION: GENERATED FROM BACTERIA PCR PRODUCT

<400> SEQUENCE: 2

```
gctcgtgacc ctcttgtttc ggcgttttat cgcgaacggt ggcgaattcg tatctgcgcg      60
tgtcatcggc tttgagactg aaggtagggc gcttaaaggc attacaacca cgaacggcgt     120
tcgctaattc gctaggcgat ga                                              142
```

<210> SEQ ID NO 3
<211> LENGTH: 504
<212> TYPE: DNA
<213> ORGANISM: OCHROBACTRUM ANTHROPI STRAIN LBAA
<220> FEATURE:
<223> OTHER INFORMATION: GENERATED FROM BACTERIA PCR PRODUCT

<400> SEQUENCE: 3

```
aagaccaaac aaggtgaagg agcaggcgaa agcactccgc aatctcatca agtccacggt      60
gcctctgatc aagtcattgg cggaggaggc tgatgcgagc catctgatcc gccatgaagg     120
tcatctgacc gtatatcgtg gagaagcaga cttcgccaag gaccgcggag gttgggaact     180
gcggcgtctc aacggtgttc gcacgcagat cctcagcgcc gatgcgttgc gggatttcga     240
tccgaacttg tcgcatgcgt ttaccaaggg cattcttata gaagagaacg gtcacacgat     300
taatccgcaa gggctcgtga ccctcttgtt tcggcgtttt atcgcgaacg gtggcgaatt     360
cgtatctgcg cgtgtcatcg gctttgagac tgaaggtagg gcgcttaaag gcattacaac     420
cacgaacggc gttctggccg ttgatgcagc ggttgtcgca gccggcgcac actcgaaatc     480
acttgctaat tcgctaggcg atga                                            504
```

<210> SEQ ID NO 4
<211> LENGTH: 454
<212> TYPE: DNA
<213> ORGANISM: OCHROBACTRUM ANTHROPI STRAIN LBAA
<220> FEATURE:
<223> OTHER INFORMATION: GENERATED FROM BACTERIA PCR PRODUCT

<400> SEQUENCE: 4

```
aagaccaaac aaggtgaagg agcaggcgaa agcactccgc aatctcatca agtccacggt      60
gcctctgatc aagtcattgg cggaggaggc tgatgcgagc catctgatcc gccatgaagg     120
```

-continued

| | |
|---|---|
| tcatctgacc gtatatcgtg gagaagcaga cttcgccaag gaccgcggag gttgggaact | 180 |
| gcggcgtctc aacggtgttc gcacgcagat cctcagcgcc gatgcgttgc gggatttcga | 240 |
| tccgaacttg tcgcatgcgt ttaccaaggg cattcttata gaagagaacg gtcacacgat | 300 |
| taatccgcaa gggctcgtga ccctcttgtt tcggcgtttt atcgcgaacg gtggcgaatt | 360 |
| cgtatctgcg cgtgtcatcg gctttgagac tgaaggtagg gcgcttaaag cattacaac | 420 |
| cacgaacggc gttcgctaat cgctaggcg atga | 454 |

<210> SEQ ID NO 5
<211> LENGTH: 22
<212> TYPE: DNA
<213> ORGANISM: OCHROBACTRUM ANTHROPI STRAIN LBAA
<220> FEATURE:
<223> OTHER INFORMATION: GENERATED FROM BACTERIA PRIMER

<400> SEQUENCE: 5

| | |
|---|---|
| aagaccaaac aaggtgaagg ag | 22 |

<210> SEQ ID NO 6
<211> LENGTH: 20
<212> TYPE: DNA
<213> ORGANISM: OCHROBACTRUM ANTHROPI STRAIN LBAA
<220> FEATURE:
<223> OTHER INFORMATION: GENERATED FROM BACTERIA PRIMER

<400> SEQUENCE: 6

| | |
|---|---|
| tcatcgccta gcgaattagc | 20 |

<210> SEQ ID NO 7
<211> LENGTH: 30
<212> TYPE: DNA
<213> ORGANISM: OCHROBACTRUM ANTHROPI STRAIN LBAA
<220> FEATURE:
<223> OTHER INFORMATION: GENERATED FROM BACTERIA PRIMER

<400> SEQUENCE: 7

| | |
|---|---|
| tcatcgccta gcgaattagc gaacgccgtt | 30 |

<210> SEQ ID NO 8
<211> LENGTH: 20
<212> TYPE: DNA
<213> ORGANISM: OCHROBACTRUM ANTHROPI STRAIN LBAA
<220> FEATURE:
<223> OTHER INFORMATION: GENERATED FROM BACTERIA PRIMER

<400> SEQUENCE: 8

| | |
|---|---|
| gctcgtgacc ctcttgtttc | 20 |

<210> SEQ ID NO 9
<211> LENGTH: 6
<212> TYPE: DNA
<213> ORGANISM: OCHROBACTRUM ANTHROPI STRAIN LBAA
<220> FEATURE:
<223> OTHER INFORMATION: GENERATED FROM BACTERIA PRIMER

<400> SEQUENCE: 9

| | |
|---|---|
| tcatcg | 6 |

<210> SEQ ID NO 10
<211> LENGTH: 19
<212> TYPE: DNA
<213> ORGANISM: Unknown
<220> FEATURE:
<223> OTHER INFORMATION: GENERATED FROM BACTERIA -continued

```
<400> SEQUENCE: 10
taatacgact cactatagg                                          19

<210> SEQ ID NO 11
<211> LENGTH: 20
<212> TYPE: DNA
<213> ORGANISM: Unknown
<220> FEATURE:
<223> OTHER INFORMATION: GENERATED FROM BACTERIA

<400> SEQUENCE: 11
ctatttaggt gacactatag                                         20

<210> SEQ ID NO 12
<211> LENGTH: 17
<212> TYPE: DNA
<213> ORGANISM: Unknown
<220> FEATURE:
<223> OTHER INFORMATION: GENERATED FROM BACTERIA

<400> SEQUENCE: 12
caggaaacag ctatgac                                            17
```